US006838128B1

(12) United States Patent
Wand et al.

(10) Patent No.: US 6,838,128 B1
(45) Date of Patent: Jan. 4, 2005

(54) HIGH POLARIZATION DOPANTS FOR FERROELECTRIC LIQUID CRYSTAL COMPOSITIONS

(75) Inventors: Michael Wand, Boulder, CO (US); Xin Hua Chen, Erie, CO (US)

(73) Assignee: Displaytech, Inc., Longmont, CO (US)

( * ) Notice: Subject to any disclaimer, the term of this patent is extended or adjusted under 35 U.S.C. 154(b) by 278 days.

(21) Appl. No.: 10/068,557

(22) Filed: Feb. 5, 2002

(51) Int. Cl.⁷ .................. C09K 19/34; C09K 19/42; C07D 307/56; C07D 239/24; C07D 405/02

(52) U.S. Cl. .............. 428/1.1; 252/299.01; 252/299.61; 252/299.62; 252/299.63; 252/299.66; 252/299.67; 544/329; 544/333; 546/268; 546/283; 549/313; 549/318; 549/319

(58) Field of Search ............... 252/299.61, 299.62, 252/299.63, 299.66, 299.67, 299.01; 544/329, 333; 546/268–283; 549/313, 318, 319; 428/1.1

(56) References Cited

U.S. PATENT DOCUMENTS

| | | | |
|---|---|---|---|
| 4,212,762 A | 7/1980 | Dubois et al. ............... 252/299 |
| 4,367,924 A | 1/1983 | Clark et al. .................. 350/334 |
| 4,490,278 A | 12/1984 | Shubert et al. .......... 252/299.63 |
| 4,874,544 A | 10/1989 | Yong et al. .............. 252/299.61 |
| 4,886,619 A | 12/1989 | Janulis ..................... 252/299.1 |
| 4,886,622 A | 12/1989 | Miyazawa et al. ....... 252/299.61 |
| 4,943,384 A | 7/1990 | Sucrow et al. .......... 252/299.61 |
| 4,952,335 A | 8/1990 | Furukawa et al. ...... 252/299.61 |
| 5,051,506 A | 9/1991 | Wand et al. .................. 544/289 |
| 5,055,221 A | 10/1991 | Scheuble et al. ....... 252/299.61 |
| 5,061,814 A | 10/1991 | Wand et al. .................. 549/560 |
| 5,062,691 A | 11/1991 | Tristani-Kendra et al. .... 359/56 |
| 5,064,566 A | 11/1991 | Hopf et al. .............. 252/299.61 |
| 5,071,589 A | 12/1991 | Dübal et al. ............. 252/299.61 |
| 5,082,587 A | 1/1992 | Janulis ................... 252/299.01 |
| 5,082,589 A | 1/1992 | Buchecker et al. ..... 252/299.63 |
| 5,110,497 A | 5/1992 | Suzuki et al. ................. 252/299 |
| 5,130,048 A | 7/1992 | Wand et al. .................. 252/299 |
| 5,138,010 A | 8/1992 | Keller et al. .................. 528/26 |
| 5,167,855 A | 12/1992 | Wand et al. ............ 252/299.01 |
| 5,168,381 A | 12/1992 | Walba ......................... 359/53 |
| 5,169,556 A | 12/1992 | Mochizuki et al. ..... 252/299.62 |
| 5,178,791 A | 1/1993 | Wand et al. ............. 252/299.65 |
| 5,178,793 A | 1/1993 | Vohra et al. ............ 252/299.61 |
| 5,180,520 A | 1/1993 | Wand et al. ............. 252/299.61 |
| 5,180,521 A | 1/1993 | Eidenschink et al. .. 252/299.61 |
| 5,190,692 A | 3/1993 | Coates et al. ........... 252/299.63 |
| 5,250,219 A | 10/1993 | Mori et al. .............. 252/299.61 |
| 5,254,747 A | 10/1993 | Janulis ....................... 568/650 |
| 5,262,082 A | 11/1993 | Janulis et al. .......... 252/299.01 |
| 5,271,864 A | 12/1993 | Wand et al. ............. 252/299.61 |
| 5,275,757 A | 1/1994 | Mineta et al. ........... 252/299.61 |
| 5,278,680 A | 1/1994 | Karasawa et al. ............. 359/40 |
| 5,286,409 A | 2/1994 | Dübal et al. ............. 252/299.61 |
| 5,322,639 A | 6/1994 | Kawabata et al. ...... 252/299.62 |
| 5,327,273 A | 7/1994 | Beresnev et al. ........... 359/104 |
| 5,338,482 A | 8/1994 | Sakaguchi et al. ...... 252/299.61 |
| 5,340,497 A | 8/1994 | Wächtler et al. ........ 252/299.61 |
| 5,340,498 A | 8/1994 | Arai et al. ............... 252/299.65 |
| 5,346,646 A | 9/1994 | Kawabata et al. ...... 252/299.62 |
| 5,346,647 A | 9/1994 | Kelly et al. ............. 252/299.63 |

(List continued on next page.)

FOREIGN PATENT DOCUMENTS

| | | |
|---|---|---|
| DE | 3906040 | 9/1989 |
| DE | 3928267 | 2/1991 |
| DE | 4315867 | 11/1994 |

(List continued on next page.)

OTHER PUBLICATIONS

US 6,030,547, 2/2000, Hasegawa et al. (withdrawn)
Arnett, K.E. et al., "Technique For Measuring Electronic-Based Electro–Optic Coefficients of Ferroelectric Liquid Crystals" (1995), *Mat. Res. Soc. Symp. Proc.* 392:135–146.

(List continued on next page.)

*Primary Examiner*—Shean C Wu
(74) *Attorney, Agent, or Firm*—Greenlee, Winner and Sullivan, P.C.

(57) ABSTRACT

The invention relates to chiral nonracemic liquid crystal compounds which are useful as components in liquid crystal compositions to impart high polarization to the mixture. The materials of this invention can be combined with liquid crystal host materials to impart improved properties to mixtures. Chiral nonracemic compounds of this invention can function as additives or dopants in host materials to impart chirality into an LC material. Most generally the invention provides mixtures containing one or more chiral nonracemic dopants which have a chiral nonracemic tail that is an optionally substituted α-ester γ-lactone of the formula:

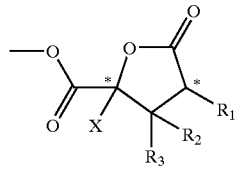

Formula I where * indicates a chiral carbon; $R_1$ is a straight-chain or branched alkyl or alkenyl group wherein one or more non-neighboring carbon atoms can be replaced with an oxygen atom and wherein one or more carbons can be substituted with one or more halogens; $R_2$ and $R_3$, independently of one another, can be hydrogen, a halogen or a lower alkyl or alkenyl group; and X is hydrogen or a lower alkyl group. LC compounds having a chiral nonracemic tail of this general formula have large dipoles (and large spontaneous polarization ($P_s$)) and when doped into hosts such as achiral smectic C FLC hosts, lead to improved switching speeds of the FLC materials.

44 Claims, No Drawings

U.S. PATENT DOCUMENTS

| | | | |
|---|---|---|---|
| 5,348,685 A | 9/1994 | Mochizuki et al. | 252/299.62 |
| 5,352,379 A | 10/1994 | Nishiyama et al. | 252/299.62 |
| 5,367,391 A | 11/1994 | Johno et al. | 359/56 |
| 5,374,375 A | 12/1994 | Yui et al. | 252/299.65 |
| 5,377,033 A | 12/1994 | Radcliffe | 359/75 |
| 5,378,394 A | 1/1995 | Dübal et al. | 252/299.61 |
| 5,378,396 A | 1/1995 | Yui et al. | 252/299.65 |
| 5,380,460 A | 1/1995 | Wand et al. | 252/299.6 |
| 5,389,287 A | 2/1995 | Nishiyama et al. | 252/299.01 |
| 5,391,319 A | 2/1995 | Junge et al. | 252/299.01 |
| 5,393,458 A | 2/1995 | Kelly | 252/299.01 |
| 5,399,291 A | 3/1995 | Janulis et al. | 252/299.01 |
| 5,399,701 A | 3/1995 | Janulis | 546/298 |
| 5,417,883 A | 5/1995 | Epstein et al. | 252/299.01 |
| 5,422,037 A | 6/1995 | Wand et al. | 252/299.61 |
| 5,427,829 A | 6/1995 | Mochizuki et al. | 428/1 |
| 5,437,812 A | 8/1995 | Janulis et al. | 252/299.01 |
| 5,445,763 A | 8/1995 | Schlosser et al. | 252/299.61 |
| 5,453,218 A | 9/1995 | Wand et al. | 252/299.01 |
| 5,455,697 A | 10/1995 | Coles et al. | 359/103 |
| 5,457,235 A | 10/1995 | Wand et al. | 568/65 |
| 5,474,705 A | 12/1995 | Janulis et al. | 252/299.01 |
| 5,482,650 A | 1/1996 | Janulis et al. | 252/299.01 |
| 5,498,368 A | 3/1996 | Coles | 252/294.67 |
| 5,529,718 A | 6/1996 | Hornung et al. | 252/299.61 |
| 5,534,190 A | 7/1996 | Johno et al. | 252/299.65 |
| 5,539,555 A | 7/1996 | Wand et al. | 359/100 |
| 5,543,078 A | 8/1996 | Walba et al. | 252/299.65 |
| 5,547,604 A | 8/1996 | Coles et al. | 252/299.01 |
| 5,568,299 A | 10/1996 | Yoshihara et al. | 359/100 |
| 5,583,682 A | 12/1996 | Kitayama et al. | 349/172 |
| 5,585,036 A | 12/1996 | Wand et al. | 252/299.01 |
| 5,595,682 A | 1/1997 | Goodby et al. | 252/299.01 |
| 5,596,434 A | 1/1997 | Walba et al. | 349/123 |
| 5,626,792 A | 5/1997 | Wand et al. | 252/299.01 |
| 5,629,428 A | 5/1997 | Schlosser et al. | 546/303 |
| 5,637,256 A | 6/1997 | Walba et al. | 252/299.66 |
| 5,653,913 A * | 8/1997 | Nakamura et al. | 252/299.01 |
| 5,658,491 A | 8/1997 | Kistner et al. | 252/299.01 |
| 5,658,493 A | 8/1997 | Walba et al. | 252/299.01 |
| 5,660,762 A | 8/1997 | Ito et al. | 252/299.67 |
| 5,695,683 A | 12/1997 | Takeichi et al. | 252/299.61 |
| 5,702,637 A | 12/1997 | Johnson et al. | 252/299.61 |
| 5,719,653 A | 2/1998 | Minato et al. | 349/156 |
| 5,723,069 A | 3/1998 | Mineta et al. | 252/299.67 |
| 5,728,864 A | 3/1998 | Motoyama et al. | 560/59 |
| 5,739,885 A | 4/1998 | Mochizuki et al. | 349/135 |
| 5,744,060 A | 4/1998 | Tarumi et al. | 252/299.63 |
| 5,748,164 A | 5/1998 | Handschy et al. | 345/89 |
| 5,750,214 A | 5/1998 | Ito et al. | 428/1 |
| 5,753,139 A | 5/1998 | Wand et al. | 252/299.01 |
| 5,770,108 A | 6/1998 | Totani et al. | 252/299.61 |
| 5,808,800 A | 9/1998 | Handschy et al. | 359/630 |
| 5,827,448 A | 10/1998 | Konuma et al. | 252/299.61 |
| 5,855,812 A | 1/1999 | Radcliffe et al. | 252/299.01 |
| 5,855,813 A | 1/1999 | Coles et al. | 252/299.5 |
| 5,856,815 A | 1/1999 | Mochizuki et al. | 345/97 |
| 5,858,273 A | 1/1999 | Asaoka et al. | 252/299.4 |
| 5,861,108 A | 1/1999 | Ishida et al. | 252/299.62 |
| 5,861,109 A | 1/1999 | Goodby et al. | 252/299.65 |
| 5,866,036 A | 2/1999 | Wand et al. | 252/299.6 |
| 5,888,420 A | 3/1999 | Sakai et al. | 252/299.01 |
| 5,922,242 A | 7/1999 | Saishu et al. | 252/299.62 |
| 5,928,562 A | 7/1999 | Kistner et al. | 252/299.6 |
| 5,932,136 A | 8/1999 | Terada et al. | 252/299.01 |
| 5,936,689 A | 8/1999 | Saishu et al. | 349/123 |
| 5,938,973 A | 8/1999 | Motoyama et al. | 252/299.65 |
| 5,942,155 A | 8/1999 | Coles et al. | 252/299.64 |
| 5,943,112 A | 8/1999 | Mochizuki et al. | 349/173 |
| 5,949,391 A | 9/1999 | Saishu et al. | 345/50 |
| 5,951,914 A | 9/1999 | Matsumoto et al. | 252/299.67 |
| 5,968,413 A | 10/1999 | Mine et al. | 252/299.65 |
| 5,972,241 A | 10/1999 | Johnson et al. | 252/299.61 |
| 5,972,243 A | 10/1999 | Mine et al. | 252/299.65 |
| 5,976,409 A | 11/1999 | Mineta et al. | 252/299.65 |
| 5,980,780 A | 11/1999 | Motoyama et al. | 252/299.64 |
| 5,985,172 A | 11/1999 | Motoyama et al. | 252/299.64 |
| 6,001,278 A | 12/1999 | Matsumoto et al. | 252/299.65 |
| 6,002,042 A | 12/1999 | Mine et al. | 560/66 |
| 6,007,737 A | 12/1999 | Nishiyama et al. | 252/299.01 |
| 6,018,070 A | 1/2000 | Ito et al. | 560/76 |
| 6,019,911 A | 2/2000 | Hirano et al. | 252/299.62 |
| 6,045,720 A | 4/2000 | Shundo et al. | 252/299.61 |
| 6,051,639 A | 4/2000 | Mehl et al. | 524/205 |
| 6,057,006 A | 5/2000 | Kirsch et al. | 428/1 |
| 6,057,007 A | 5/2000 | Amano et al. | 428/1 |
| 6,084,649 A | 7/2000 | Amano et al. | 349/96 |
| 6,106,908 A | 8/2000 | Duffy et al. | 428/1.1 |
| 6,139,771 A | 10/2000 | Walba et al. | 252/299.01 |
| 6,413,448 B1 | 7/2002 | Wand et al. | 252/299.63 |

FOREIGN PATENT DOCUMENTS

| | | | |
|---|---|---|---|
| EP | 0 307 880 | 3/1989 | |
| EP | 0 331 091 | 9/1989 | |
| EP | 0 356 672 | 3/1990 | |
| EP | 0 401 522 | 12/1990 | |
| EP | 405868 A2 | 1/1991 | C09K/19/42 |
| EP | 255236 B1 | 5/1994 | C09K/19/20 |
| EP | 0 545 409 B1 | 3/1996 | |
| EP | 425304 B1 | 7/1996 | G02F/1/137 |
| EP | 579545 B1 | 3/1997 | G02F/1/1337 |
| EP | 0 769 543 A1 | 4/1997 | C09K/19/02 |
| EP | 736078 B1 | 6/1998 | C09K/19/04 |
| JP | 1213390 A2 | 8/1989 | C09K/19/46 |
| JP | 63039286 | 8/1989 | C09K/19/46 |
| JP | 01041845 | 12/1989 | C07C/43/20 |
| JP | 01053791 | 12/1989 | C07D/319/06 |
| JP | 01071776 | 12/1989 | C07D/239/26 |
| JP | 1316339 A2 | 12/1989 | C07C/43/20 |
| JP | 1316367 A2 | 12/1989 | C07D/239/26 |
| JP | 1316372 A2 | 12/1989 | C07D/319/06 |
| JP | 4-193873 * | 7/1992 | |
| JP | 4-208277 * | 7/1992 | |
| JP | 8-82778 A | 3/1996 | G02F/1/13 |
| JP | 8-113784 | 5/1996 | C09K/19/54 |
| JP | 228128 A | 8/2000 | H01H/13/04 |
| WO | 86/06401 | 11/1986 | |
| WO | 87/05015 | 8/1987 | |
| WO | 87/05018 | 8/1987 | |
| WO | WO 89/10356 | 11/1989 | C07D/213/06 |
| WO | WO 91/00897 | 1/1991 | C09K/19/34 |
| WO | WO 97/36908 | 10/1997 | C07F/7/21 |
| WO | WO 99/33814 | 7/1999 | C07D/239/26 |
| WO | WO 00/31210 | 6/2000 | C09K/19/04 |

OTHER PUBLICATIONS

Bezborodov, V.S. et al., "Synthesis, mesomorphic properties and potential applications of aryl esters of 4–n–alkcyclohexene–1–carboxylic acids in electrooptic displays," (1989) CAPLUS 1989:240081 (abstract only).

Bezborodov et al. (1989), "Synthesis, mesomorphic properties and potential applications of aryl esters of 4–n–alkycyclohexene–1–carboxylic acids in electrooptic displays," *Liq. Cryst.* 4(2):209–215.

Blinov L.M. and Tournilhac, F., "Infra–Red Dichroism of Mesophases Formed By Polyphilic Molecules. 1. Development of the Technique and Study of Compounds With One Long Perfluorinated Tail" (1993), *Molecular Materials* 3:93–111.

Booth, C.J. et al., "The ferro–, ferri– and antiferro–electric properties of a series of novel 2– or 3–substituted–alkyl 4–(4'–dodecyloxybiphenyl–4–carbonyloxy)–benzoate esters" (1996), *Liquid Crystals* 20(6):815–823.

Booth, C.J. et al., "Achiral–swallow–tailed materials with 'antiferroelectric–like' structure and their potential use in antiferroelectric mixtures" (1996), *Liquid Crystals* 20(4):387–392.

CAPLUS 1998: 624749.

CAPLUS 2001: 305417.

Chandani, A.D.L. et al., "Novel Phases Exhibiting Tristable Switching" (Jul. 1989), *Jpn. J. App. Phys.* 28:L1261–1264.

Chandani, A.D.L. et al., "Antiferroelectric Chiral Smectic Phases Responsible for the Tristable Switching in MHPOB-C"(Jul. 1989), *Jpn. J. App. Phys.* 28:L1265–1268.

Chandani, A.D.L. et al., "Tristable Switching in Surface Stabilized Ferroelectric Liquid Crystals with a Large Spontaneous Polarization" (May 1988), *Jpn. J. App. Phys.* 27(5):L729–732.

Clark, N.A. and Lagerwall, S.T., "Submicrosecond bistable electro–optic switching in liquid crystals"(Jun. 1980), *Appl. Phys. Lett.* 36:899–901.

Clark, N.A. et al., Electro–Optic Characteristics of de Vries Tilted and Smectic Liquid Crystals: Analog Behavior in the Smectic A* and Smectic C* Phases (2002) *Appl. Phys. Lett.* 80:4097–99.

Coates, D. and Greenfield, S. (1991), "Liquid crystal compositions comprising 4–alkyl–4'–(o–fluorophenethyl)bicyclohexanes for supertwisted nematic electrooptical display devices," Chem. Abstracts, vol. 115, Abstract No. 115: 82430v. p. 752.

Dawson, D.J. et al., (1987) "Cocyclotrimerization of Aryl Acetylenes: Substituent Effects on Reaction Rate" *Am. Chem. Soc. Sym.* 346 Ch 38:446–456.

de Vries, A., "Experimental Evidence Concerning Two Different Kinds Of Smectic C To Smectic A Transitions" (1977), *Mol. Cryst. Liq. Cryst. (Letters)* 41:27–31.

de Vries, A., "The Implications of the Diffuse–Cone Model for Smectic *A* and *C* Phases and *A–C* Phase Transitions" (1979), *Mol. Cryst. Liq. Cryst (Letter).* 49:179–185.

Drzewinski, W. et al. "Antiferroelectric Liquid Crystals with Fluorinated Parts of Terminal Chains" CAPLUS 1998:624787 (abstract only).

Edgar, K. J. and Falling, S.N., "An Efficient and Selective Method for the Preparation of Iodophenols" (1990) *Org. Chem.* 55:5287–5291.

Escher, C. et al. (1991), "Liquid crystal compositions for electrooptical display devices," *Chem. Abstracts* vol. 115, Abstract No. 115:194312q, p. 775.

Fleming, F. F. and Jiang, T., "Unsaturated Nitriles: Optimized Coupling of the Chloroprene Grignard Reagent[1] with ω–Bromonitriles" *J. Org. Chem.* (1997) 62:7890–7891.

Fung, B.M. et al. (1989), "Liquid crystals containing a cyclohexene ring," *Mol. Cryst. Liq. Cryst. Lett.* 6(6):191–196.

Gorecka, E. et al., "Molecular Orientational Structures in Ferroelectric, Ferrielectric and Antiferroelectic Smectic Liquid Crystal Phases as Studied by Conoscope Observation" (Jan. 1990), *Jap. J. Appl. Phys.* 29(1):131–137.

Hartmann, W., "Uniform SSFLC Director Pattern Switching" (1998), *Ferroelectrics* 85:67–77.

Heinemann, S. et al., "Synthesis and Dielectric Investigations of New Swallow–Tailed Monomers and Polymers" (1993), *Mol. Cryst. Liq. Cryst.* 237:277–283.

Heinemann, S. et al., "Competition between dipolar and steric interactions in swallow–tailed compounds" (1993), *Liquid Crystals* 13(3):373–380.

Hide, F. et al., "Dynamic Polarized Infared Spectroscopy of Electric Field–Induced Molecular reorientation in a Chiral Smectic–A Liquid Crystal" (Sep. 1995), *Phys. Rev. Lett.* 75(12):2344–2347.

Inui, S. et al., "Thresholdless antiferroelectricity in liquid crystals and its application to displays" (1996), *J. Mater. Chem.* 6(4):671–673.

Inukai, T. et al., "Dicyanohydroquinone cyclohexanecarboxylic acid esters," (1980) CAPLUS 1989:604304 (abstract only).

Johno, M. et al., "Correspondence between Smectic Layer Switching and DC Hysteresis of Apparent Tilt Angle in an Antiferroelectric Liquid Crystal Mixture" (Jan. 1990), *Jap. J. Applied Phys.* 29(1):L111–114.

Johno, M. et al., "Smectic Layer Switching by an Electric Field in Ferroelectric Liquid Crystals Cells" (Jan. 1989), *Jpn. J. App. Phys.* 28(1):L119–120.

Kagawa, A. et al., "Fast Response Time STN=LCD with High Contrast Ratio" (1995), Proceedings of the 15th International Display Research Conference 177–180.

Kelly, S.M. (1991), "Four unit linking groups. II. Some novel smectic C materials," Liq. Cryst. 10(2):243–260.

Klopper et al., "IR–Modulation Spectroscopy on the Collective Dynamics of Free–Standing Ferroelectic Liquid Crystalline Films" (Jan. 1997), J. Physique II France 7(1):57–67.

Li et al. (1991) "Liquid crystals with a chiral core: cyclohexene carboxylates," *Mol. Cryst. Liq. Cryst.* 199:379–386.

Matsumoto, T. et al., "A novel property caused by frustration between ferroelectricity and its application to liquid crystal displays—frustoelectricity V –shaped switching" (Sep. 1999) *J. Mater. Chem.* 9:2051–2080.

McMullen, W. et al., "Theoretical Studies of the Isotropic-Nematic Interface" *Mol. Cryst. Liq. Cryst.*(1991) 198:107–117.

Mikami, K. et al., "Diastereotropic Phenomena for the Appearance of SmCA*Phase in α–Trifluoromethyl–β–methyl–substituted Liquid Crystaline Molecules" (1996) *Chemistry Letters*.

Mikami, K. et al., "Binaphthol–Titanium Complex–Catalyzed Fluoral–Ene Reaction with Vinyl Sulfides for Asymmetric Synthesis of Diastereomeric α–Trifluoromethyl–βmethyl Carbinols: Diastereomer Switch of Antiferreoelectric of Ferroelectric Properties of Diastereomeric Liquid–Crystalline Systems[1]" (Sep. 1996) *SYNLETT* 837–838.

Mochizuki, A. et al., "A High Contrast and High Transmittance Multiplexing SSFLC Display Utilizing Naphthalene Base Liquid Crystal Materials" (1991), *Ferroelectrics* 122:37–51.

Mochizuki, A. et al., "Zigzag defect free alignment and good bistability of surface stabilized $S_c$* Cells" (1991), *Ferroelectrics* 113:353–359.

Mottram, N.J. and Elston, S.J, "Preliminary communication Thresholdless switching induced by polar anchoring in antiferroelectric liquid crystals" (1999) *Liquid Crystals* 26(12):1853–1856.

Nakagawa, A., A Hysteresis Model for Antiferroelectric $SmC_{A^*}$ (Aug. 1991), *Jap. J. App. Phys.* 30(8):1759–1764.

Nohira, H. et al. (1989), "Optically active compounds and liquid–crystal compositions and devices containing them," *Chem. Abstracts* vol. 111, Abstract No. 111:15479x, p. 571.

Ostrovskii, B.I. et al., "Evidence of Tilted Dimeric Mesophase for Terminally Polar Polyphilic Mesogens" (1995), *J. Physique II France* 5(7):979–1001.

Park, B. et al., "Molecular motion in a smectic liquid crystal showing V–shaped switching as studied by optical second–harmonic generation"(Apr. 1999)*Physical Review E* 59(4) 3815–3818.

Perova, T.S. et al., "Study Of The Molecular Orientation in A Chiral Smectic Liquid Crystal Mixture using Infrared Dichroism" (1996), *Ferroelectrics* 180(1–4):105–115.

Redmond, M. et al., "Ferroelectric and Electroclinic Characterization of a New Organic Siloxane Bimesogen." (1993) *Ferroelectrics* 148:323–336.

Rieker, T.P. et al., "'Chevron' Local Layer Structure in Surface–Stabilized Ferroelectric Smectic–C Cells" (Dec. 1987), *Physical Rev. Letts.* 59(23):2658–2661.

Rudquist, J.P. et al., "The case of thresholdless antiferroelectricity: polarization–stabilized twisted SmC* liquid crystals give V–shaped electro–optic response" (1999), *J. Mater. Chem.* 9:1257–1261.

Sakaigawa, A. and Nohira, H., "Properties of Ferroelectric Liquid Crystal Mixtures Containing Fluorine Substituted Compounds"(1993) *Ferroelectrics* 148:71–78.

Schmitt, K. et al., "Strongly non–linear optical ferroelectric liquid crystals for frequency doubling" (1993) *Liquid Crystals* 14(6) 1735–1752.

Seomun, S.S. et al., "Evolution of Switching Characteristics from Tristable to V–Shaped in an Apparently Antiferroelectric Liquid Crystal" (Jun. 1997), *J. Appl. Phys.* 36:3586–3590.

Shibata, T. et al., "Liquid Crystal Composition," (1996) CAPLUS 1997:179123 (abstract).

Takanishi, Y. et al., "Spontaneous Formation of QuasiBookshelf Layer Structure in New Ferroelectric Liquid Crystals Derived from a Naphthalene Ring" (Jun. 1990), *Jap. J. Applied Phys.* 29(6):L984–L986.

Takatsu, H. et al. (1984), "Synthesis and Some Properties of Nematic Compounds Containing Three Ring Systems," *Mol. Cryst. Liq. Cryst.* 111:311–319.

Takehara, S. et al. (1991), "A ferroelectric chiral smectic liquid crystal composition containing a high temperature liquid crystal: trans–1–(hetero)aryloxymethyl–4–alkylcyclohexane," *Chem. Abstracts*, vol. 115, Abstract No. 115: 102976h, p. 735.

Takehara S. et al. (1991), "Ferroelectric liquid crystal compositions," *Chem. Abstracts*, vol. 115, Abstract No. 115:82385j, p. 750.

Takiguchi, T. et al. (1991), "Ferroelectric liquid crystal composition," *Chem. Abstracts*, vol. 115, Abstract No. 115:82387m, p. 750.

Tuffin, R. P. et al., "Non–Chiral Compounds Exhibiting Alternating Tilt Smectic Phases" (1995) *Mol. Cryst. Liq. Cryst.* 260:51–67.

Zhuang, Z., "Interfacial Interactions, Director Configurations and Layer Structures of Surface Stabilized Ferroelectric Liquid Crystals" (1991), *Ph.D. Thesis, University of Colorado, Boulder CO.* 105 pages.

* cited by examiner

HIGH POLARIZATION DOPANTS FOR FERROELECTRIC LIQUID CRYSTAL COMPOSITIONS

BACKGROUND OF THE INVENTION

The present invention relates generally to liquid crystal compounds and compositions and to devices employing liquid crystal compositions. The invention more specifically relates to chiral nonracemic compounds useful as dopants in ferroelectric liquid crystal compositions to impart high polarization and fast switching speed. The dopants combine a rod-like mesogenic-core with a chiral nonracemic tail and an achiral tail.

Several types of smectic LC materials have been investigated for rapid switching, view-angle enhancement and higher contrast, including surface-stabilized ferroelectric LCs (SSFLCs), deformed helix ferroelectric LCs (DHFLCs) and antiferroelectric LCs (AFLCs). Recently, smectic materials exhibiting thresholdless or more properly V-shaped switching LCs (VLCs) have been described (Inui, S. et al. (1996) J. Mater. Chem. 6(4):671–673; Seomun, S. S. et al. (1997) Jpn. J. Appl. Phys. 36:3580–3590).

Liquid crystal compositions exhibit one or more LC phases. LC compositions may be composed of one or more components. Components of LC compositions may exhibit liquid crystal phases, have latent liquid crystal phases or be compatible with (not suppress) liquid crystal phases in the liquid crystal composition.

To achieve full color imaging in ferroelectric liquid crystal (FLC) displays, the FLC material is required to have fast switching speed. It is known in the art that switching speed is proportional to the viscosity of and inversely proportional to the spontaneous polarization (Ps) of the FLC material. It is also known that switching speed can be improved by doping a small percentage of high Ps compounds into an achiral smectic C host Chiral FLC compounds and components of LC mixtures generally consist of a rigid mesogenic core having one or more directly or indirectly linked alicyclic or aromatic rings (which may be fused aromatic rings) and achiral and chiral tails distributed on either side of the mesogenic core, e.g.:

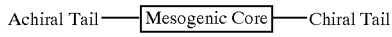

Large Ps can be achieved by modifying one of these three building blocks, but among them, developing new chiral tails with large dipoles which can be oriented in the smectic C phase of a host FLC, is the most efficient way to increase the Ps of the LC composition.

SUMMARY OF THE INVENTION

The invention relates to chiral nonracemic liquid crystal compounds which are useful as components in liquid crystal compositions to impart high polarization to the mixture. The materials of this invention can be combined with liquid crystal host materials to impart improved properties to mixtures. Chiral nonracemic compounds of this invention can function as additives or dopants in host materials to impart chirality into an LC material.

Most generally the invention provides mixtures containing one or more chiral nonracemic dopants which have a chiral nonracemic tail that is an optionally substituted α-ester γ-lactone of the formula:

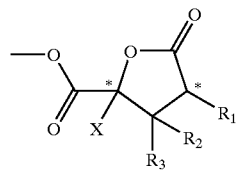

Formula I where * indicates a chiral carbon; $R_1$ is a straight-chain or branched alkyl or alkenyl group wherein one or more non-neighboring carbon atoms can be replaced with an oxygen atom and wherein one or more carbons can be substituted with one or more halogens; $R_2$ and $R_3$ independently of one another, can be hydrogen, a halogen or a lower alkyl or alkenyl group; and X is hydrogen or a lower alkyl group. LC compounds having a chiral nonracemic tail of this general formula have large dipoles (and large spontaneous polarization ($P_s$)) and when doped into hosts such as achiral smectic C FLC hosts, lead to improved switching speeds of the FLC materials.

This chiral nonracemic tail imparts high polarization to liquid crystal compositions. Liquid crystal compounds having a chiral non-racemic γ-lactone ester tail bonded to a mesogenic core impart high polarization to liquid crystal compositions containing them. The chiral non-racemic γ-lactone ester tail can be combined with any known mesogenic core, particularly, rod-like, linear cores.

Typically mesogenic cores include one to about three aromatic or alicyclic rings, Aromatic rings include both 5- and 6-member aromatic rings and fused aromatic rings, such as napthatene rings. Ore or two carbons in a 5- or 6-member aromatic ring can be replaced with a heteroatom, such a O, N or S. Alicyclic rings include cyclohexane and cyclohexene rings wherein one of the carbons atoms of the ring can be replaced with a Heteroatom or in which one of the $CH_2$ of the ring can be replaced with C=O. The carbons of the aticyclic ring or the aromatic ring can be substituted with lower alkyl groups, halides, CN groups or nitro groups. Mesogenic cores also include a dioxane ring, an optionally substituted phenyl ring, an optionally substituted cyclohexyl ring and an optionally substituted cyclohexenyl ring in which one or two carbons may be optionally substituted with the same or different heteroatoms, such as O, N or S.

Mesogenic cores can comprise one aromatic ring, two aromatic rings or three aromatic rings. Mesogenic cores can comprise two or three cyctohexane rings, cyclohexene rings or a combination of both. Mesogenic cores can contain a combination of aromatic rings and cyclohexane or cyclohexene rings. The aromatic or alicyclic rings of a mesogenic core can comprise linking groups between the rings Linking groups can include a single bond, a —CH2—CH2—, —CH=CH, —C≡C—, O S. CO, COO, —CH2—O—.

More specifically, the invention relates to chiral nonracemic compounds of general formula:

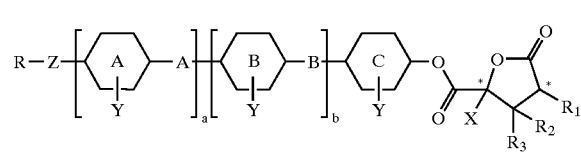

Formula II where *, $R_1$, $R_2$, $R_3$, and X are as described for Formula I;
R is selected from the group consisting of:

(1) an achiral straight chain or branched silane or siloxane having one or more silicon atoms and which may be substituted with one or more halogens;

(2) an achiral linear or branched perfluorinated or partially fluorinated alkyl group ($R^F$);

(3) an achiral linear, cyclic or branched perfluorinated or partially fluorinated ether group;

(4) an achiral linear or branched ether having one or more oxygen atoms and which may be substituted with one or more halogens;

(5) an achiral alkyl, alkenyl or alkynyl group which may be substituted with one of more halogens; and (6) a straight chain or branched thioether having one or more sulfur atoms and which may be substituted with one or more halogens.

and where:

Z is a linker selected from the group consisting of O, CO, OOC, COO, S or a single bond; core rings A, B and C and linker moieties A and B together represent a mesogenic core, and can be aromatic or alicyclic; if aromatic, one or two ring carbons can be replaced with a nitrogen; or if alicyclic, rings can contain 3–10 carbon atoms and optionally can contain a double bond, wherein one or two $CH_2$ of the alicyclic ring can be replaced with a nitrogen, sulfur, or oxygen atom, or a C=O group, each ring can be a fused ring system;

Y represents up to four substituents on a giver ring when the ring is aromatic and up to 20 substituents when the ring is alicyclic, where substituents are selected from a halide, CN, $NO_2$, alkyl or alkoxy groups;

Linkers A and B, independently, are selected from the group consisting of a single bond, —COO—, —OOC——$CH_2$—$CH_2$—, —$OCH_2$—, —$CH_2$—O—, —CH=CH—(cis or trans); —C≡C—, and —CH=CH—CH=CH—(cis or trans);

and where a and b are integers that are 0 or 1 to indicate the absence or presence of the groups in brackets and where a+b is 1 or 2.

In a specific embodiment, compounds of this invention have the formula:

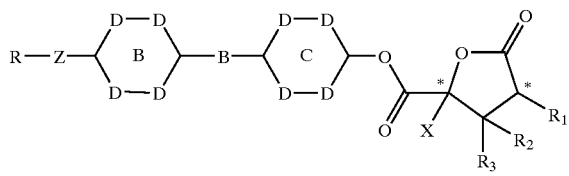

Formula III where R, $R_1$, $R_2$ $R_3$, X, linker B, and rings B and C are as defined above and each D, independent of other D's, can be CH, $CH_2$, C—$CH_3$, CH—$CH_3$, a nitrogen atom, CY or CHY, where Y is a CN, $NO_2$, an alkyl, a perhaloalkyl (e.g., perfluoroalkyl), or a halide, (e.g., fluorine). Rings B and C can be alicyclic or aromatic and B and C that are aromatic can be fused ring systems, such as naphthalene. One of rings B or C can also be a fused ring system that is partially aromatic, such as a dehydronapthalene ring system. In particular embodiments, both of rings B and C are aromatic, or one of rings B or C is aromatic and the other or rings B or C is alicyclic, particularly a cyclohexane or cyclohexene ring. In preferred embodiments: (1) all D's are CH; (2) one or two D's are N and the remaining D's are CH; (3) one or two D's are CF and the remaining D's are CH; (4) one or two D's are N, one or two D's are CF and the remaining D's are CH; (3) all D's on one ring are $CH_2$ and one, two or three D's on the other ring can be N or CF; (4) all D's on one ring are $CH_2$ and all D's on the other ring are CH; (5) one or two D's on one ring are CF and one D on the other ring is C—$CH_3$.

In a further specific embodiment, compounds of this invention have the formula:

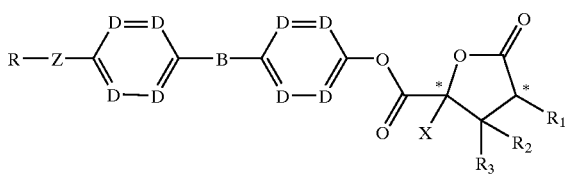

Formula IV where R, Z, B, X, $R_1$ $R_2$ and $R_3$ are as defined above, and where each D independent of other D's can be CH or CY as defined above or a nitrogen atom and all other variables are as defined above. In preferred compounds of Formula IV, all D's are CH or one or two D's can be CF or nitrogen with the remaining D's being CH. In preferred embodiments, the core is a phenylpyrimidine, a phenylpyridine, phenylbenzoate, or biphenyl.

In another specific embodiment, compounds of this invention can have the formula:

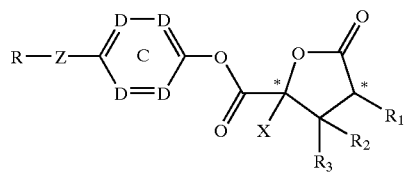

Formula V where the variables R, Z, C, X $R_1$, $R_2$ and $R_3$ are as defined above, and where each D, independent of other D's, can be CH, CY or a nitrogen. In preferred compounds of Formula V, all D's are CH or one or two D's can be CF or nitrogen with the remaining D's being CH.

In yet another specific embodiment, compounds of this invention can have the formula:

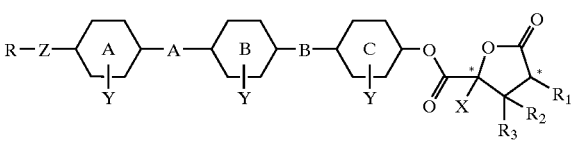

Formula VI where the variables are as defined in Formula II above. In particular embodiments of Formula VI the core can be (1) an optionally substituted terphenyl, where the preferred substitution is one or two F's; (2) a core in which A or C is a cyclohexane or cyclohexene ring and the remaining rings are aromatic; (3) a core in which A or C is a cyclohexane or cyclohexene and the remaining rings are selected from phenyl rings, phenyl rings substituted with one or two F's, pyrimidine rings or pyridine rings; or (4) a core in which A or C is a cyclohexane or cyclohexene and the remaining two rings represent a phenylpyrimidine, a phenylpyridine, a phenyl benzoate or a biphenyl.

Compounds of Formulas II–VI are useful in the preparation of LC and FLC compositions which in turn are useful in various optical device applications.

Particular subsets of compounds of Formula II–VI include those in which:

R is an achiral alkyl, alkenyl or alkynyl group having from 3 to about 20 carbon atoms in which one or more of the non-neighboring carbons can be replaced with an oxygen, or in which one or more of the carbons is substituted with one of more halogens;

R is $R^F$ where $R^F$ is an achiral linear or branched perfluorinated or partially fluorinated alkyl group;

$R^F$ has the formula: $C_nF_{2n+1}C_mH_{2m}$ wherein n is an integer ranging from 1 to about 10 and m is an integer ranging from 1 to about 10;

$R^F$ has the formula: $C_nF_{2n+1}C_mH_{2m}$ wherein n is an integer ranging from 1 to about 20 and m is an integer ranging from 0 to about 20;

$R^F$ is $C_4F_9C_4H_8$;

R is an achiral silane.

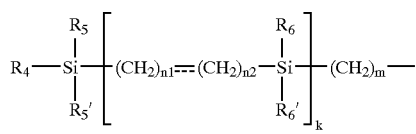

where:

$R^4$ is a straight chain or branched alkyl or alkenyl group having one or more carbon atoms and $R_5$, $R_{5'}$, $R_6$ and $R_{6'}$, independently of one another, are alkyl groups having from 1–6 carbon atoms;

n1 and m are integers from 1 to about 20;

n2 can be zero or an integer from 1 to 20 where the dashed line indicates a possible double or triple bond;

k is 0 or an integer from 1 to 10;

X is H;

X is a lower alkyl group;

X is CH,

Z is O;

Z is a single bond;

the mesogenic core is

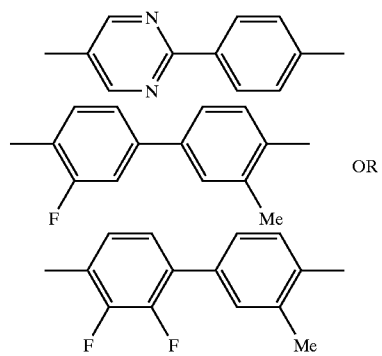

As used herein the term alkyl refers generally to straight-chain and branched alkyl groups. Alkyl groups can include lower alkyl groups (those having from 1–6 carbon atoms) and higher alkyl groups (those having about 7 or more carbon atoms), unless otherwise noted. The term alkoxy group refers to groups having a terminal oxygen atom (e.g., —O-alkyl). For example, alkoxy tail groups are attached to the core via the terminal oxygen. The alkyl portion of an alkoxy group includes straight-chain and branched alkyl groups and unless otherwise noted includes lower alkyl and higher alkyl groups. Alkyl groups, including those of alkoxy group, typically have less than 20 carbons and preferably, dependent upon the specific structure, have 12 or fewer carbon atoms. In compounds where alkyl or alkoxy tail groups are specified, preferred alkyl groups have from 5 to 12 carbon atoms and more preferred alkyl groups have 6 to 10 carbon atoms.

As used herein the term alkene refers generally to any group containing one or more double bonds. The alkene tails of this invention as specified in Formulas I–VI contain a single double bond. Alkene tails include alkene-oxy tails, ie., —O-alkene, in which the alkene group has a terminal oxygen atom which forms the bond to the core. In general the double bond of the alkene tail can be positioned anywhere in the chain, but preferably is located 2 or more carbons from the end of the tail attached to the core. The alkene may contain an omega double bond, but the double bond is more preferably located away from the ends of the tail. The double bond may be in the cis or trans configuration.

The term alicyclic generally refers to alkyl or alkene groups that contain a cyclic portion. An alicyclic group can be a saturated ring or unsaturated ring, such as a cyclohexane or cyclohexene ring. Alicyclic rings can contain one or more (typically one) heteroatoms, e.g., O, N or S, in place of ring $CH_2$ groups. Further, one or more (typically one) ring $CH_2$ groups can be replaced with C=O groups. Alicyclic groups of the cores of this invention are optionally substituted (unless otherwise noted). Preferred substituents include lower alkyl groups, lower alkene groups, halogens, CN and $NO_2$ groups. Preferred halogen substituents are fluorines. In general, all but two aromatic ring positions (e.g., the positions for linkages to tails or to other core rings) can carry non-hydrogen substituents. However, more typically one or two ring positions (in addition to the linkages to the tails or other cores) can be substituted.

The term aromatic generally refers to a group containing at least one aromatic ring, e.g., a phenyl ring. Aromatic rings typically are five or six-member aromatic rings. Aromatic rings can also include fused aromatic rings, such as naphthalene or dehydronapthalene rings (see Scheme 1). Scheme 1 shows some mesogenic cores useful in compounds of the invention. An aromatic ring can contain one or more (typically one or two) heteroatoms, e.g., O, N or S. Aromatic groups of the cores of this invention are optionally substituted (unless otherwise noted)., Preferred substituents include lower alkyl groups, lower alkene groups, halogens, CN and $NO_2$ groups. Preferred halogen substituents are fluorines. In general, all but two positions on the ring can be substituted (e.g., the positions for linkages to tails or to other core rings). However, typically one to four positions of the ring can be substituted and more typically one or two ring positions (in addition to the linkages to the tails or other cores) can be substituted. Preferred substituted aromatic rings have one position substituted with a lower alkyl or alkene group, a CN group or a $NO_2$ group. Additionally preferred substituted aromatic rings have one or two positions substituted with one or two halogens, and the preferred halogen is fluorine.

The invention provides LC compositions comprising one or more of the compounds of this invention as described above. LC compositions of the invention include those that certain sufficient amounts of one or more of the compounds of this invention to have a substantial effect upon the physical or optical properties of the LC composition in which they are combined or to which they are added. A substantial effect upon the physical or optical properties of the LC compositions includes, among others, a measurable change in a LC property of the composition, for example, switching speed. LC compositions of this invention include those that contain from about 1% to 100% by weight of one or more compounds of this invention. LC compositions of this invention include those that contain 1% or more by weight of one or more of the compounds of this invention. Preferably, LC compositions of this invention contain 1% to 50% by weight of one or more compounds of this invention. More preferably, LC compositions of this invention contain 1% to 15% by weight of one or more compounds of this invention.

LC compositions of this invention include those that are ferroelectric liquid crystal compositions, particularly those that exhibit smectic phases, and more particularly those that exhibit a smectic,C phase. LC compositions of this invention exhibit smectic phases from about −10° C. to 70° C.

Any FLC host can be used as known in the art as long as the host does not interfere with the desired effect. One specific host that is used in the examples shown herein in MX6111, shown in Table 2.

LC and FLC compositions of this invention are useful in the preparation of optical devices, particularly for optical switching devices and displays. It is known to those of ordinary skill in the art how to make LC and FLC cells and devices that utilize the compositions of this invention. In particular, methods and techniques are known and available in the art for alignment of LC and FLC compositions between substrate layers to form optical elements that exhibit true bistable, near bistable, or tristable state switching or optical elements that exhibit analog behavior. Various methods and techniques for constructing LC and FLC cells and for use of such cells are known in the art and can be readily adapted for use with compositions of this invention. The compositions of this invention are particularly well suited for providing devices that can operate (in a smectic C phase, for example) over a broad temperature range.

DETAILED DESCRIPTION OF THE INVENTION

The invention relates generally to compounds that are useful as components in LC compositions. LC compositions typically contain a plurality of components, some of which exhibit LC phases alone or in combination. More preferred LC compositions are those which exhibit a desired LC phase over a temperature range that facilitates practical application of the composition in an optical device. For example, LC materials exhibiting a smectic C range around normal room temperature can be employed in device applications. Preferred LC materials will exhibit the desired LC phase over a broad, useful temperature range which facilitates device stability.

Preferred LC materials will exhibit a desired LC phase with temperature range that minimizes or avoids crystallization of components of the LC composition during operation or storage of an optical device. Compounds of this invention can improve (broaden or shift) the temperature range of desired LC phases in LC compositions to which they are added. In particular, compounds of this invention can be employed to broaden or shift the temperature range of smectic C phases of LC compositions. The compounds may also be added to lower the temperature at which crystallization of an LC composition occurs to improve storage lifetime of an LC device containing the LC composition. Improvement is assessed as lowering of the melting point of the compositions and/or as lowering of the freezing point of the mixture. A significant improvement in LC stability can be obtained with even a 2° C. lowering of melting point, if that lowering is obtained without a significant negative effect on other LC properties.

EXAMPLES

Table 1 shows the results for spontaneous polarization as measured for some compounds of this invention. Table 3 shows comparative results for lactone ether compounds. It is seen that compounds of the invention with lactone ester tails have higher polarization than lactone ether compounds. In all cases, the compounds were doped at 5% by weight in host MX 6111 shown in Table 2. Schemes 4 and 5 illustrates a number of compounds that can be combined with the chiral nonracemic compounds of this invention to provided useful mixtures Compounds illustrated therein can be prepared by methods that are well known in the art from readily available starting materials. Methods that are useful in the preparation of various LC compounds and FLC compounds are provided, for example in U.S. Pat. Nos. 5,051,506; 5,061,814; 5,130,048; 5,167,855; 5,178,791; 5,178,793; 5,180,520; 5,271,864; 5,278,680; 5,380,460; 5,422,037; 5,453,218; 5,457,235; 5,539,555; 5,543,078; 5,585,036; 5,626,792; 5,637,256; 5,658,493; 5,753,139; 5,866,036; and 6,139,771. Each of which is incorporated by reference herein for synthetic methods applicable to the synthesis of compounds of this invention. The listed patents along with U.S. Pat. Nos. 5,168,381 and 5,596,434 also provide detail of how LC and FLC compositions of this invention can be applied for the production of LC cells and optical devices.

Concurrently filed U.S. patent application Ser. Nos. 09/754,034, 09/753,749 and 09/754,033 all provide description of LC components and methods of synthesis of those components that can be combined with the chiral nonracemic compounds of this invention to provide useful FLC compositions.

In addition, chiral racemic compounds or corresponding achiral compounds of this invention can be employed as additional compatible components of FLC compositions of this invention.

Scheme 2 lists an example synthesis to prepare the chiral tails of the invention. The variables in the scheme are as described here. Other synthesis methods are well known to one of ordinary skill in the art.

Scheme 3 shows some of the more preferred compounds of the invention.

Although the description above contains many specificities, these are not intended to limit the scope of the invention, but merely to provide illustrations of some of the presently—preferred embodiments of the invention. For example, mesogenic cores other than those specifically, illustrated herein can be used in the compounds of the invention. Also, compounds other than those specifically described may be used, as known in the art to form mixtures with the compounds of the invention. Thus, the scope of the invention should be determined by the appended claims and their legal equivalents. All references cited herein are hereby incorporated by reference to the extent not inconsistent herewith.

Scheme 1
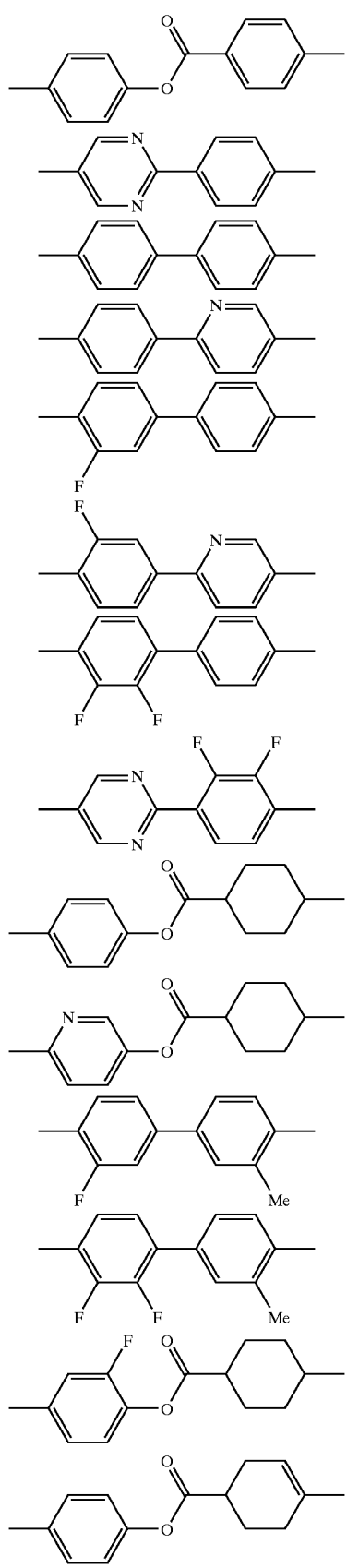
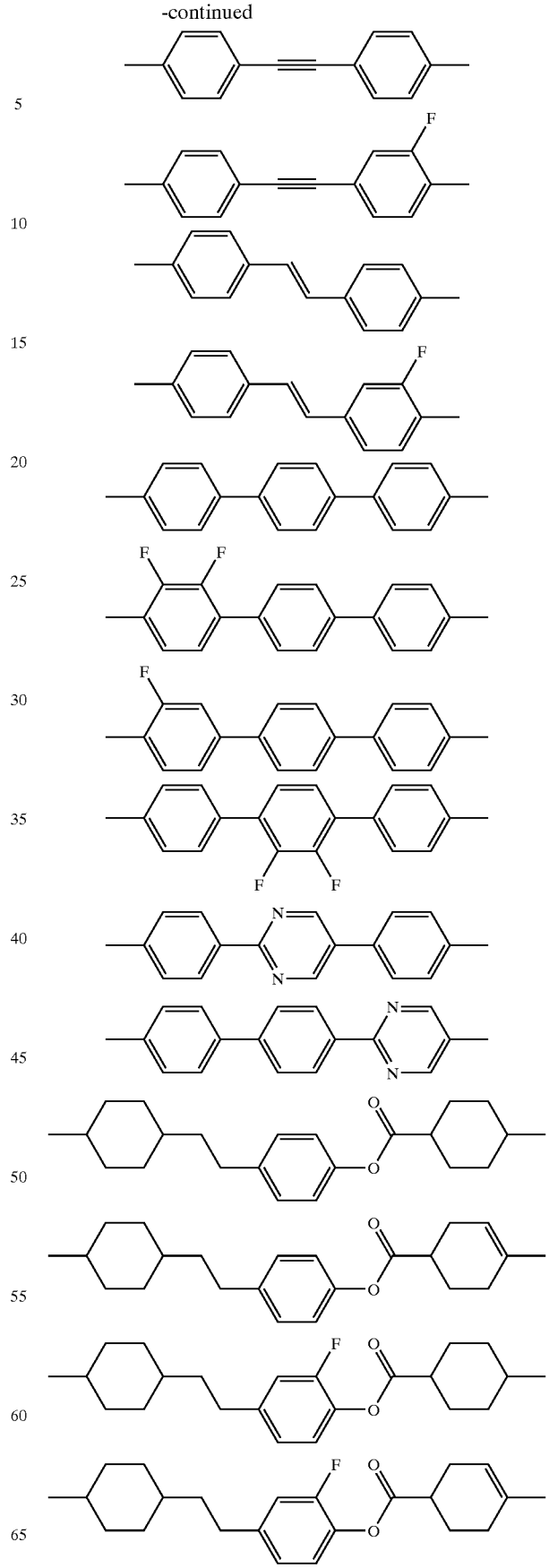

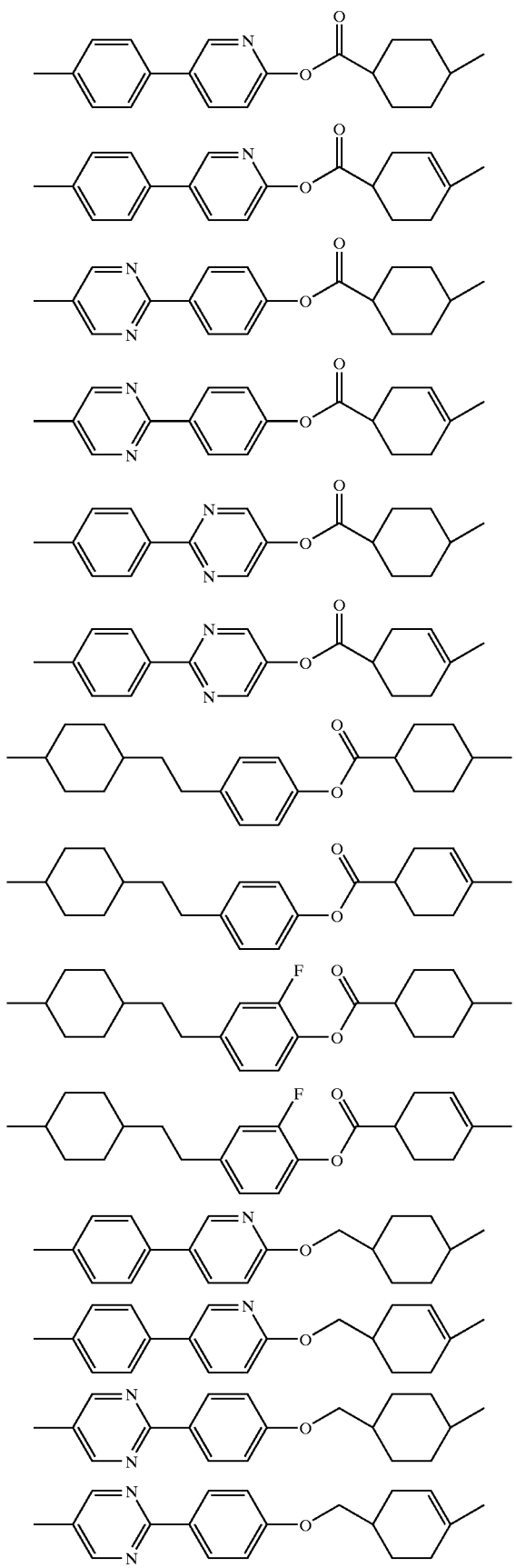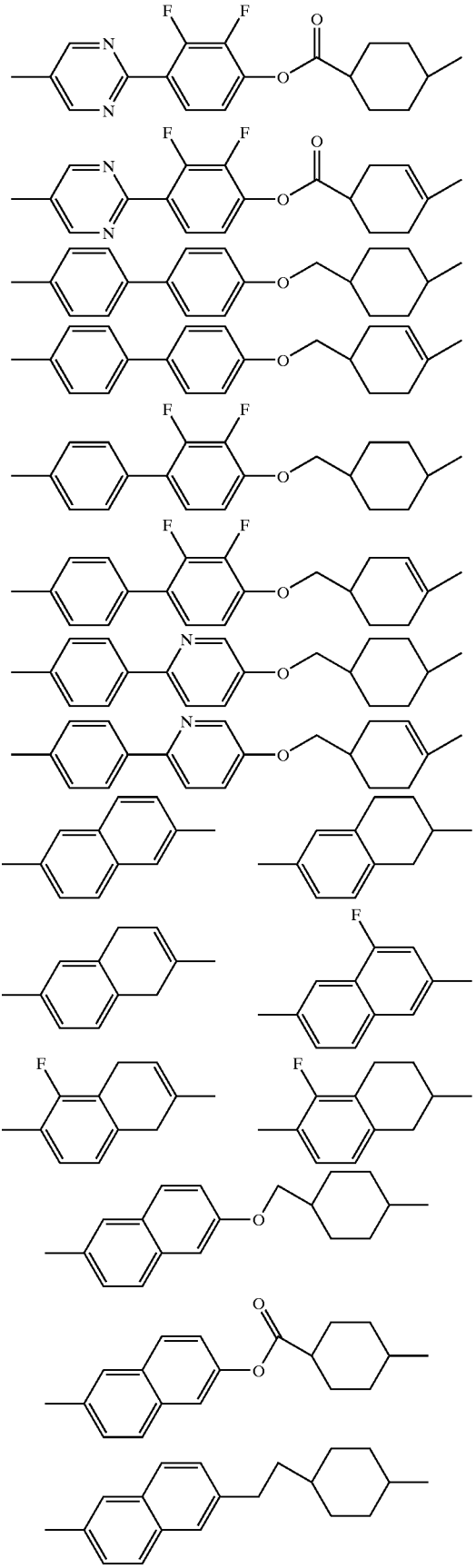

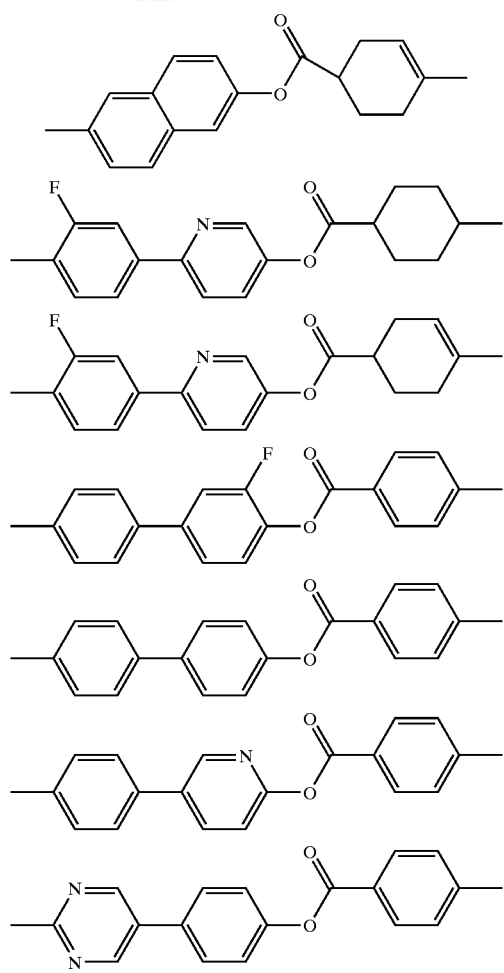
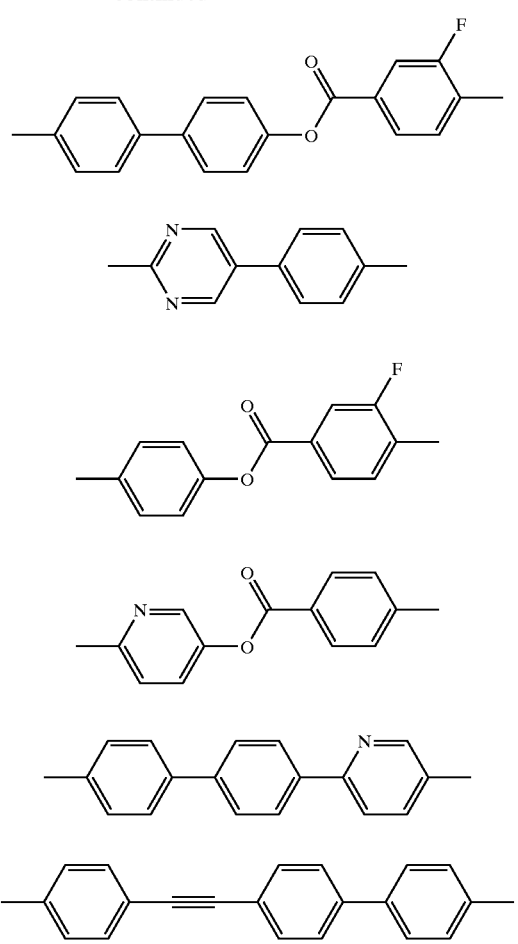
Scheme 2
Synthesis of Lactone Ester
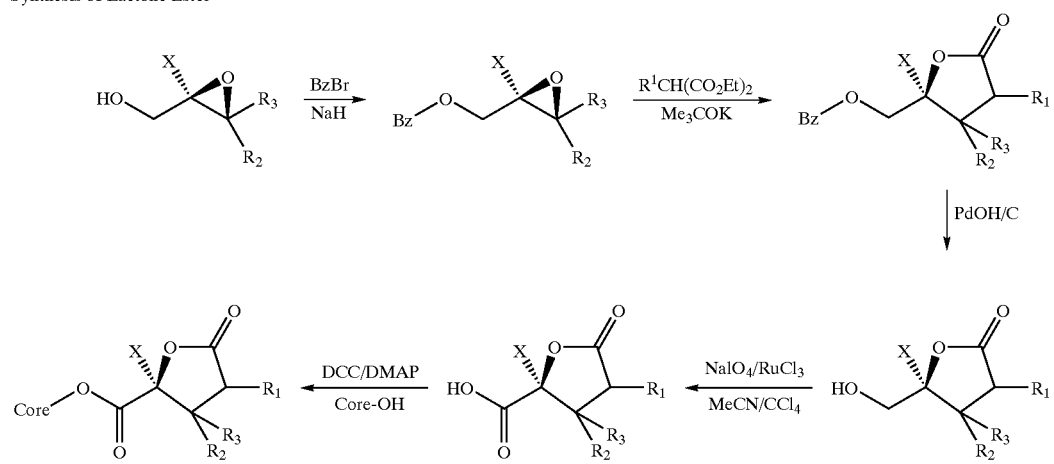

Scheme III
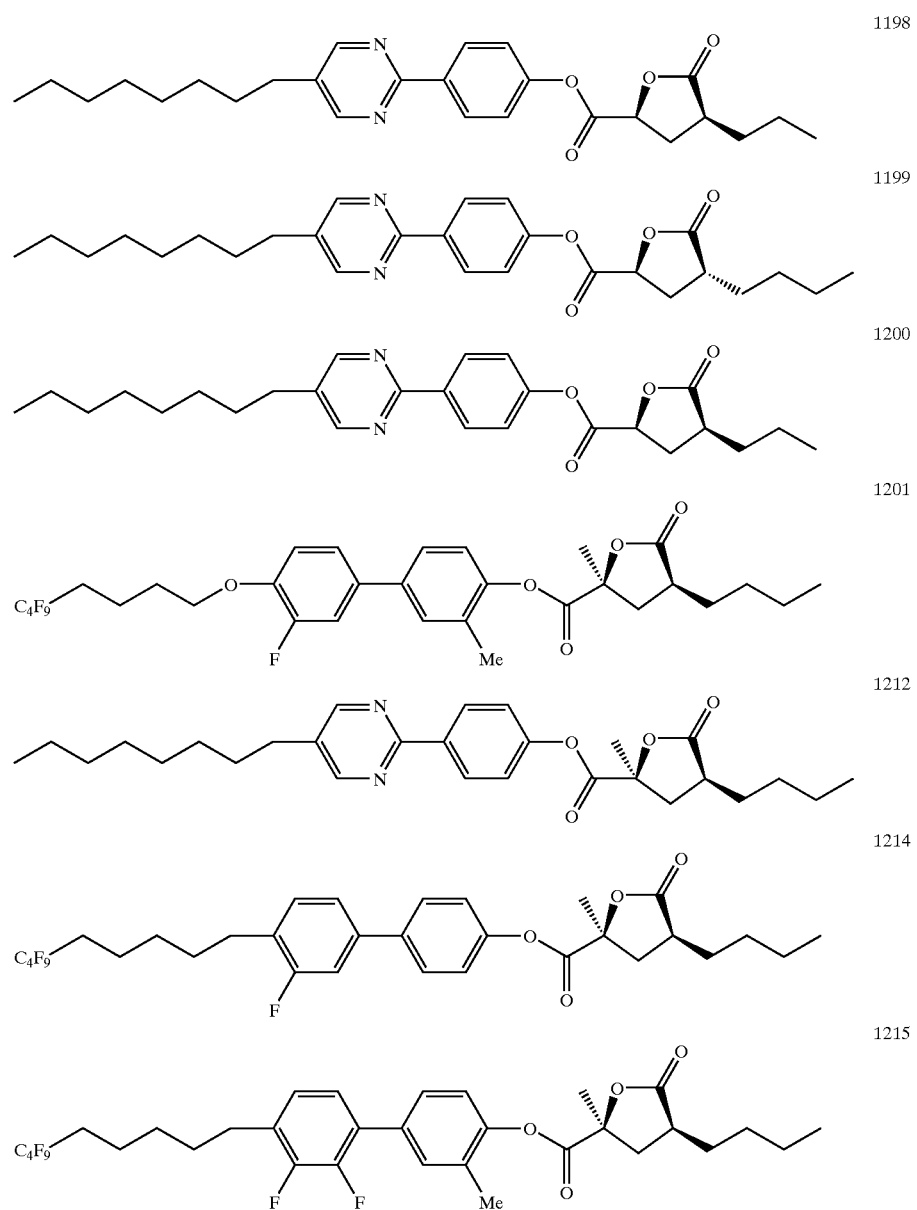
TABLE 1
| MDW | Structure | Ps (nC/cm²) |
|---|---|---|
| 1198 | 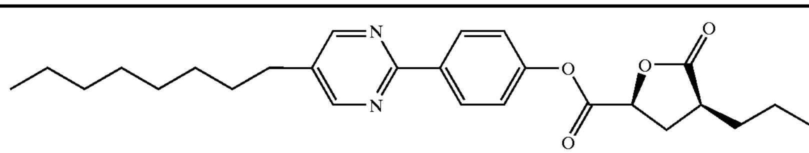 | 40.1 |
| 1201 | 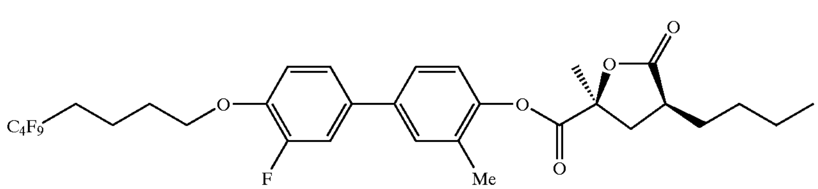 | 21.1 |

TABLE 1-continued
| MDW | Structure | Ps (nC/cm$^2$) |
|---|---|---|
| 1212 | 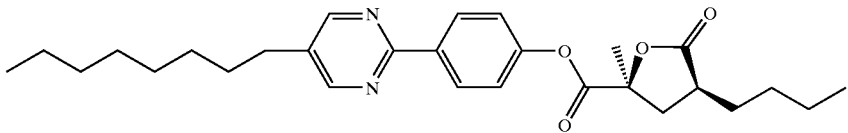 | 11.1 |
| 1215 | 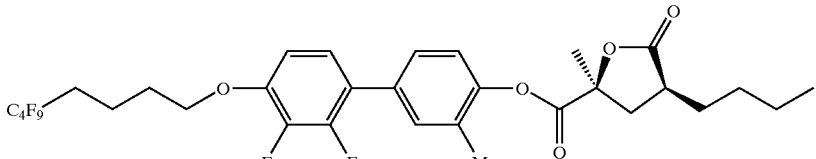 | 15 |
TABLE 2
Composition of MX 6111
| MX 6111 Structure and MDW # | % Composition |
|---|---|
| 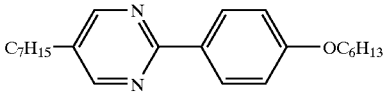<br>MDW 1 | 5.6 |
| 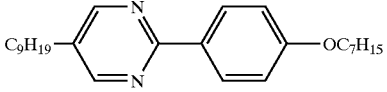<br>MDW 2 | 5.6 |
| 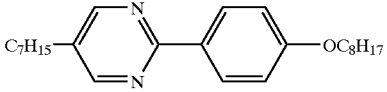<br>MDW 3 | 5.6 |
| 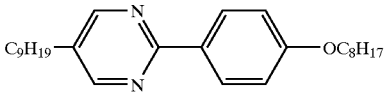<br>MDW 4 | 7.2 |
| 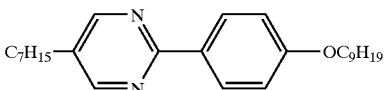<br>MDW 22 | 5.6 |
| 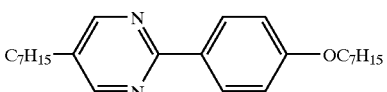<br>MDW 31 | 5.6 |

TABLE 2-continued
Composition of MX 6111
| MX 6111 Structure and MDW # | % Composition |
|---|---|
| 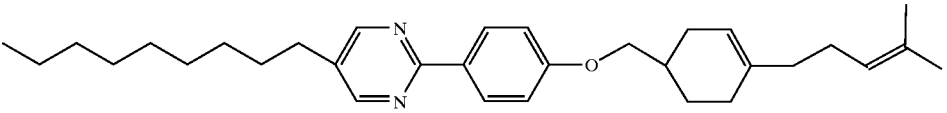 MDW 343 | 20 |
| 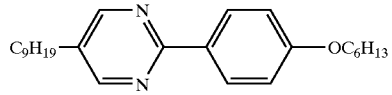 MDW 764 | 9.6 |
| 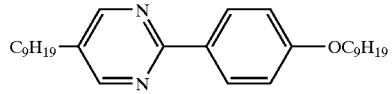 MDW 1287 | 33.6 |
TABLE 3
lactone ether comparison compounds
5% mix in MX6111
| MDW # | MIXES | Optical Phase | Ps | Elec-Rise Time |
|---|---|---|---|---|
| 1400 | 10083 | I 73.5 N 69 A 50.4 C <25 X<br>X 133 I//I 115 X | 12.9 | 125 |
| 1428 | 10084 | I 73.5 N 68.5 52 C <25 X<br>X 133 I//I 115.1 X | 12.4 | 125 |
| 1429 | 10085 | I 73.5 N 68.7 A 53.3 C <25 X<br>X 112.4 I//I 99.1 X | 5.9 | 250 |
| 1905 | 10104 | I (72.8–68.5) N 65.7 A 48 C <25 X<br>X 100 I//I 78.9 X | 15.4 | 85 |
| 1907 | 10105 | I (70.7–65) N 63 SmX 51.5 C <25 X<br>OIL | 7.4 | 165 |
| 1908 | 10106 | I (74.5–68.1) N 67.5 A 50 C <25 X<br>X 98 I//I 108 X | 14.3 | 120 |
| 1909 | 10107 | I (71–62) N 51 SmX 48 C <25 X<br>X 90 I//I 25 X | 3.5 | 357 |
1905
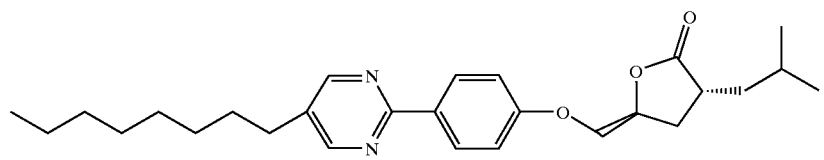
1907
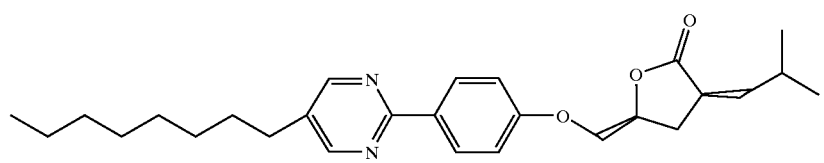
1908
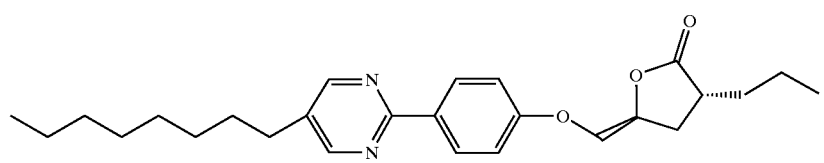

TABLE 3-continued
1909
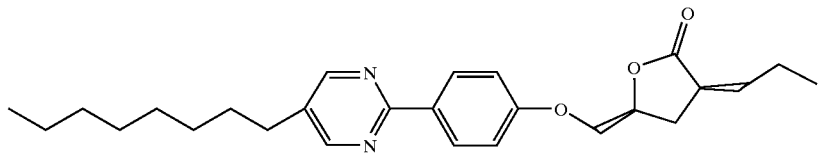
1400
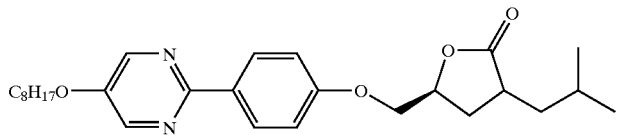
1428
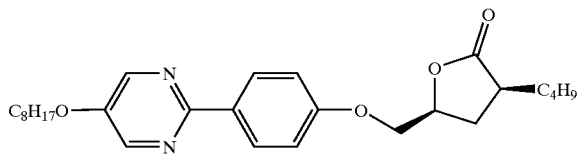
1429
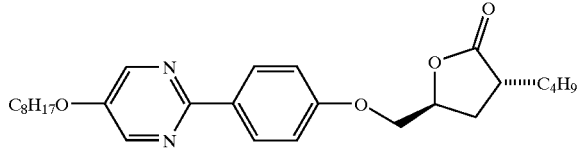
Scheme 4
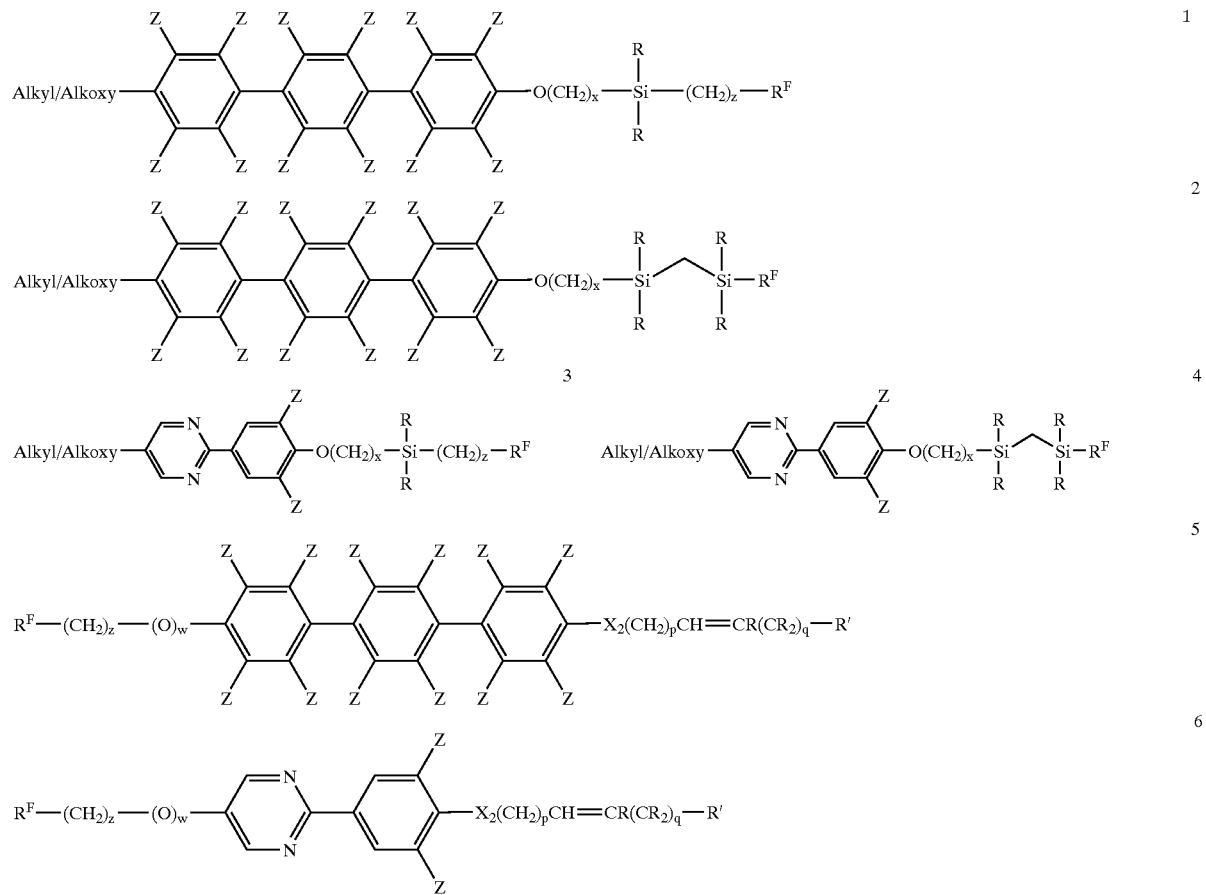

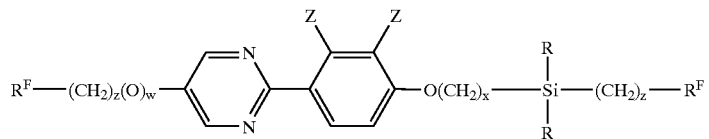
7
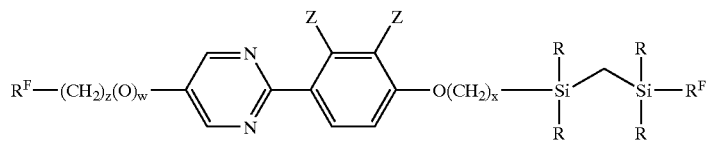
8
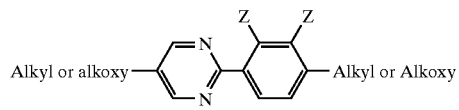
9
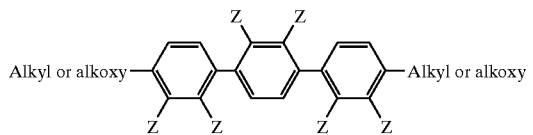
10
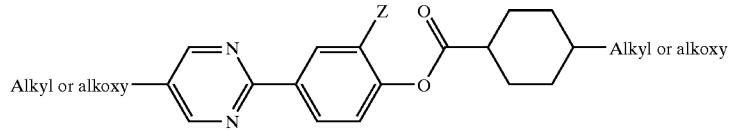
11
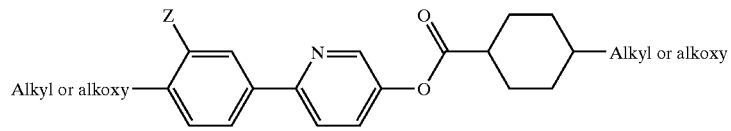
12
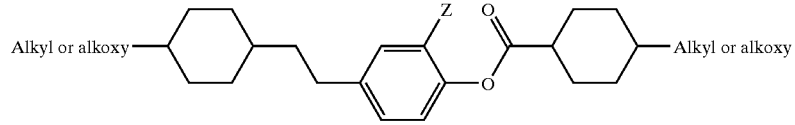
13
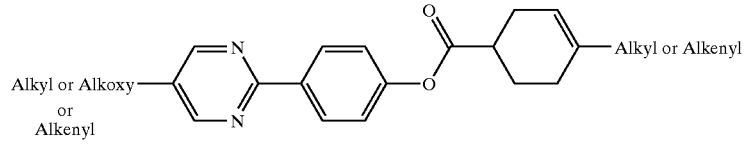
14
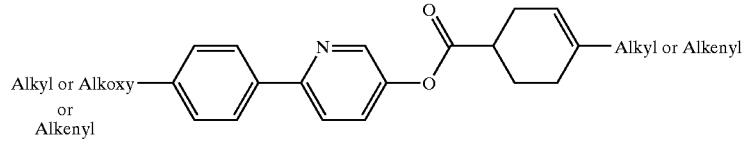
15
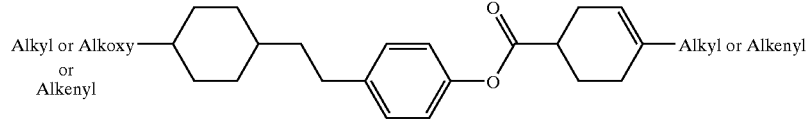
16
wherein p, x and z are integers ranging from 1 to 20, inclusive, q is 0 or an integer ranging, from 1 to 20, inclusive; w is 0 or 1; R are alkyl groups, preferably having from 1 to 6 carbon atoms; R' is an alkyl group having from 5 to 20 carbon atoms; $R^F$ is a perfluoroalkyl group; Z is H or a F; and alkyl or alkoxy groups are those that have 1 to 20 carbon atoms.

SCHEME 5

| MDW # | Structure | Phase Diagram |
|---|---|---|
| 950 | C8H17-Ph-Pyridine-O-CH2-CHF-CHF-C4H9 | X <-90 - I - 94-> |
| 987 | C4H9C4H8O-Pyrimidine-Ph-O-CH2-C(CH3)(F)-C4H9 | X <----21------ SmC* <-54- SmA <-63-I-53 -> S? -57-> |
| 644 | C10H21O-Ph-Pyrimidine-O-CH2CH2-CH(CH3)-CH2CH2-CH(CH3)2 | X <-20- N <-41-I-43-> -47-> |
| 699 | C10H21O-Ph-Pyrimidine-O-CH2CH2-CH(CH3)-CH2CH2-CH(CH3)2 | |
| 139 | C4F9C4H8O-Pyrimidine-Ph-O-C(O)-epoxide-C3H7 | X - 75-> I <-86- |
| 337 | C10H21-Pyrimidine-Ph-O-C(O)-Cy-C5H11 | X <-100- C <-105-N <-169-I |
| 1135 | C8H17O-Ph-Pyridine-O-C(O)-Cy-CH2CH2CH2-CH(CH3)2 | X <-73.5 -S?<-85- C <-104-A<-175-N <-186-I |
| 1638 | C8H17O-Ph(F)-Pyridine-O-C(O)-Cy-CH2CH2CH2-CH(CH3)2 | |
| 1458 | C5H11-Cy-CH2CH2-Ph(F)-O-C(O)-Cy-CH2CH2CH2-CH(CH3)2 | |
| 1671 | C7H15-Ph(F,F)-Ph-Ph-C5H11 | X -56-> C -106-> A -131-> N -136-> I |
| 1673 | C7H15-Ph-Ph(F,F)-Ph-C5H11 | X -37-> N -112-> I X<-24- C |

SCHEME 5-continued

| MDW # | Structure | Phase Diagram |
|---|---|---|
| 1674 | C7H15—⟨benzene⟩—⟨benzene⟩—⟨2,3-difluorobenzene⟩—C5H11 | X -66-> SI -75->C -119-> A -135->N-137-> I |
| 31 | C7H15—⟨pyrimidine⟩—⟨benzene⟩—OC7H15 | |
| 3 | C7H15—⟨pyrimidine⟩—⟨benzene⟩—OC8H17 | X -49-> A -44-> N -69.5-> I |
| 1695 | C8H17—⟨pyrimidine⟩—⟨benzene⟩—OC6H13 | |
| 5 | C8H17—⟨pyrimidine⟩—⟨benzene⟩—OC12H25 | X -43.2-> C -62.4-> A -66.8-> N -68.2-> I |
| 4 | C9H19—⟨pyrimidine⟩—⟨benzene⟩—OC8H17 | X -33-> C -60-> A -74.5-> I |
| 913 | C9H19—⟨pyrimidine⟩—⟨2,3-difluorobenzene⟩—OC7H15 | X -43-> C -50-> I <-44- <52- |
| 911 | C9H19—⟨pyrimidine⟩—⟨2,3-difluorobenzene⟩—OC9H19 | X -44-> C -52-> I <-37- <-52- |
| 374 | C8H17—⟨pyrimidine⟩—⟨benzene⟩—OC6H13 | |
| 1054 | C8H17—O—⟨benzene⟩—⟨pyridine⟩—O—C(=O)—⟨cyclohexene⟩—CH2CH2CH=C(CH3)2 | X <----- C <-135- N<-150- I -55-> Sx -82-> |
| 942 | C5H11—⟨cyclohexane⟩—CH2CH2—⟨benzene⟩—O—C(=O)—⟨cyclohexene⟩—CH2CH2CH=C(CH3)2 | |
| 576 | C10H21—⟨pyrimidine⟩—⟨benzene⟩—O—C(=O)—⟨cyclohexene⟩—CH3 | X <-35- S? <-45- C <-68- N<-107- I -50> -54-> |

SCHEME 5-continued

| MDW # | Structure | Phase Diagram |
|---|---|---|
| 1059 | C₁₀H₂₁-pyrimidine-C₆H₄-O-C(O)-cyclohexene-CH₂CH₂CH(CH₃)₂ | |
| 336 | C₁₀H₂₁-pyridine-C₆H₄-O-C(O)-cyclohexene-CH₂CH=C(CH₃)₂ | X <-27- C <-83- N<-106- I -40-> |
| 577 | C₁₀H₂₁-C₆H₄-pyrimidine-O-C(O)-cyclohexene-CH₂CH=C(CH₃)₂ | |
| 1701 | C₇H₁₅-C₆H₄-C₆H₄-C₆H₂F₂-OC₁₀H₂₀-Si(CH₃)₃ | |
| 1669 | C₇H₁₅-C₆H₄-C₆H₄-C₆H₂F₂-OC₄H₈-Si(CH₃)₂-CH₂CH₂CF₃ | |
| 1658 | C₈H₁₇O-C₆H₂F₂-C₆H₄-C₆H₄-OC₄H₈-Si(CH₃)₂-CH₂CH₂CF₃ | |
| 1592 | C₄F₉C₄H₈O-pyrimidine-C₆H₄-OC₄H₈-Si(CH₃)₂-CH₂CH₂CF₃ | |
| 1532 | C₁₀H₂₁O-pyrimidine-C₆H₄-OC₄H₈-Si(CH₃)₂-CH₂CH₂CF₃ | |
| 1632 | C₁₀H₂₁O-pyrimidine-C₆H₄-OC₄H₈-Si(CH₃)₂-CH₂CH₂C₆F₁₃ | |
| 1586 | C₄F₉C₄H₈-O-pyrimidine-C₆H₄-OC₈H₁₆-Si(CH₃)₂-CH₂-Si(CH₃)₃ | |
| 1709 | C₄F₉C₅H₁₀-pyrimidine-C₆H₄-OC₁₀H₂₀-Si(CH₃)₃ | |

SCHEME 5-continued

| MDW # | Structure | Phase Diagram |
|---|---|---|

[Structure: C4F9C4H8O-pyrimidine-phenyl-O-CH2CH2CH2CH2-CH=CH-C4H9] MDW 1597

Cr 64.9    SmC 100.4    SmA 102.4    I
   43.3         99.6          101.0

[Structure: C4F9C4H8O-pyrimidine-phenyl-O-CH2CH2-CH=CH-C3H7]

Cr 61.7    SmC 135.0    I
   57.7         134.6

[Structure: C4F9C4H8O-pyrimidine-phenyl-O-CH2CH2CH2CH2-CH=CH-CH2CH2CH3]

Cr 70.7    SmC 113.8    SmA 115.4    I
   60.7         113.8         114.6

[Structure: C4F9C4H8O-pyrimidine-phenyl-O-CH2CH2-CH=CH-CH2CH2CH2CH3]

Cr 59.0    SmC 114.2    SmA 121.0    I

[Structure: C4F9C4H8O-pyrimidine-phenyl-O-CH2CH2-CH(CH3)-CH2CH2-CH=C(CH3)2] MDW 1015

Cr 62    SmA 67    I

[Structure: C4F9C4H8O-pyrimidine-phenyl-O-CH2-cyclohexenyl-CH2CH2-CH=C(CH3)2] MDW 1028

---

We claim:

1. A liquid crystal composition comprising one or more chiral nonracemic compounds of formula:

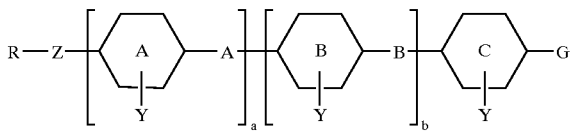

where the substituents between Z and G represent the core; where G is a chiral nonracemic optionally substituted α-ester γ-lactone of formula:

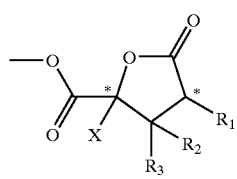

where * indicates a chiral carbon, $R_1$ is a straight-chain or branched alkyl or alkenyl group wherein one or more non-neighboring carbon atoms can be replaced with an oxygen atom and wherein one or more carbons can be substituted with one or more halogens;

$R_2$ and $R_3$, independently of one another, can be H, halogen or a lower alkyl or alkenyl group;

X is H, or a lower alkyl group;

R is selected from the group consisting of:
(1) an achiral straight chain or branched silane or siloxane having one or more silicon atoms and which may be substituted with one or more halogens
(2) an achiral linear or branched perfluorinated or partially fluorinated alkyl group ($R^F$);
(3) an achiral linear, cyclic or branched perfluorinated or partially fluorinated ether group;
(4) an achiral linear or branched ether having one or more oxygen atoms and which may be substituted with one or more halogens;
(5) an achiral alkyl, alkenyl or alkynyl group which may be substituted with one of more halogens;
(6) or a straight chain or branched thioether having one or more sulfur atoms and which may be substituted with one or more halogens.

and where:

Z is a linker selected from the group consisting of O, CO, OOC, COO, S or a single bond;

core rings A, B and C can be aromatic or alicyclic; if aromatic, one or two ring carbons can be replaced with a nitrogen; or if alicyclic, rings can contain 3–10 carbon atoms and optionally can contain a double bond, wherein one or two $CH_2$ of the alicyclic ring can be replaced with a nitrogen, sulfur, or oxygen atom, or a C=O group;

Y represents up to four substituents on a given ring when the ring is aromatic and up to 20 substituents when the ring is alicyclic, where substituents are selected from halides, CN, $NO_2$, alkyl or alkoxy;

linkers A and B, independently, are selected from the group consisting of a single bond, —COO—, —OOC—, —$CH_2$—$CH_2$—, —$OCH_2$—, —$CH_2$—O—, —CH=CH— (cis or trans); —C≡C—, and —CH=CH—CH=CH— (cis or trans);

and where a and b are integers that are 0 or 1 and where a+b is 1 or 2; wherein when X is H, R is not an achiral linear partially fluorinated ether group.

2. The liquid crystal composition of claim 1 wherein the core is selected from the group consisting of:

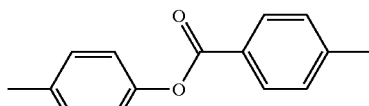

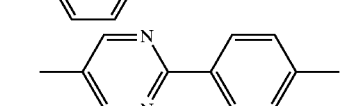

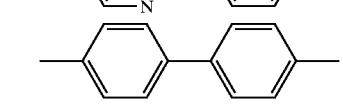

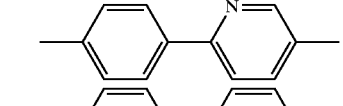

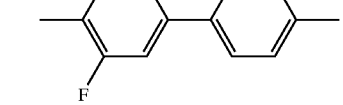

-continued

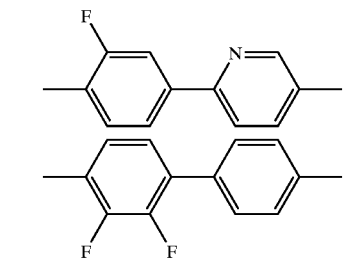

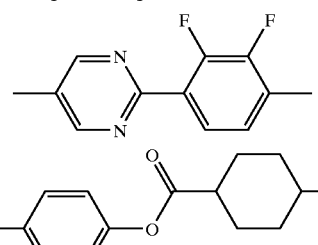

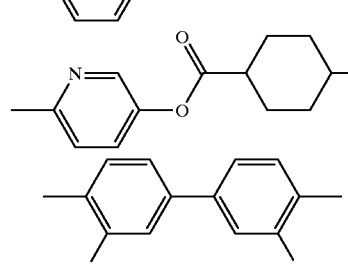

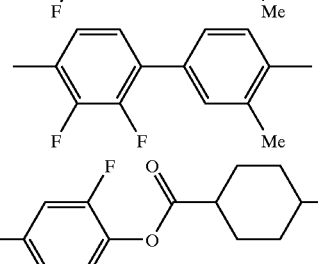

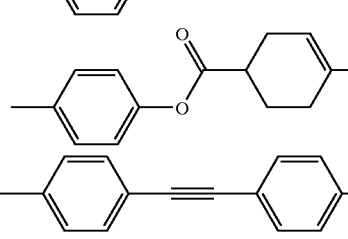

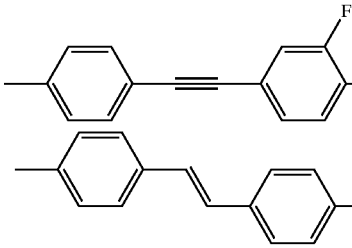

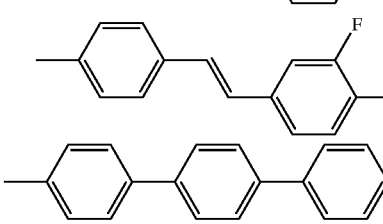

-continued
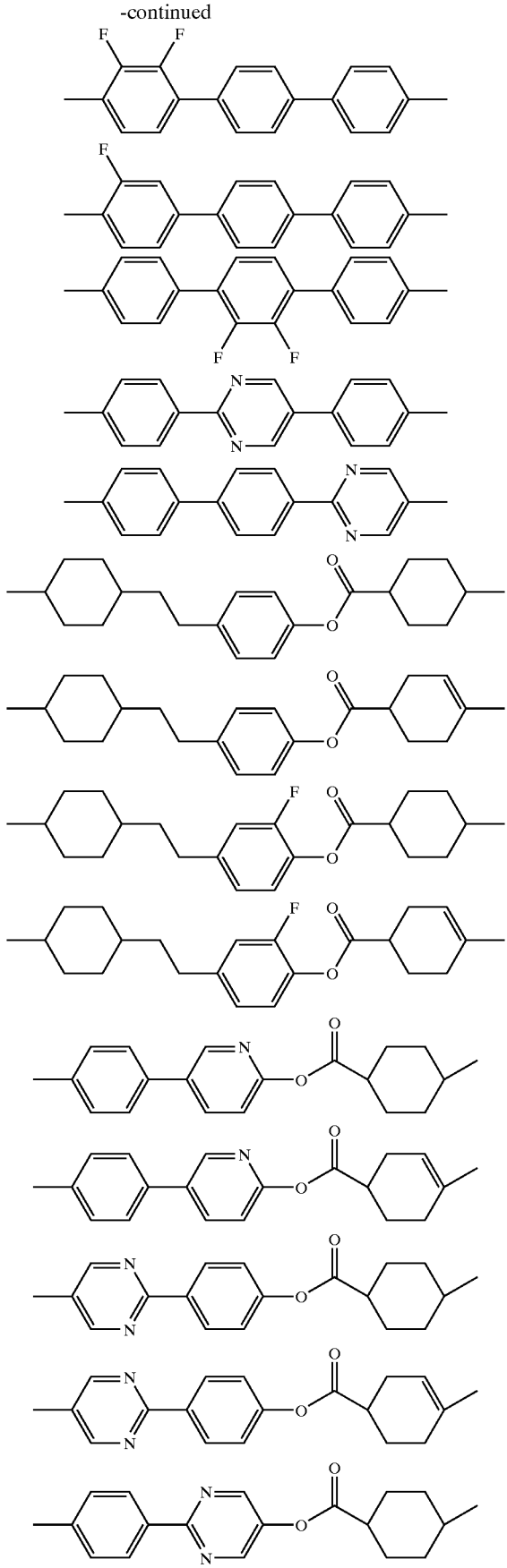
-continued
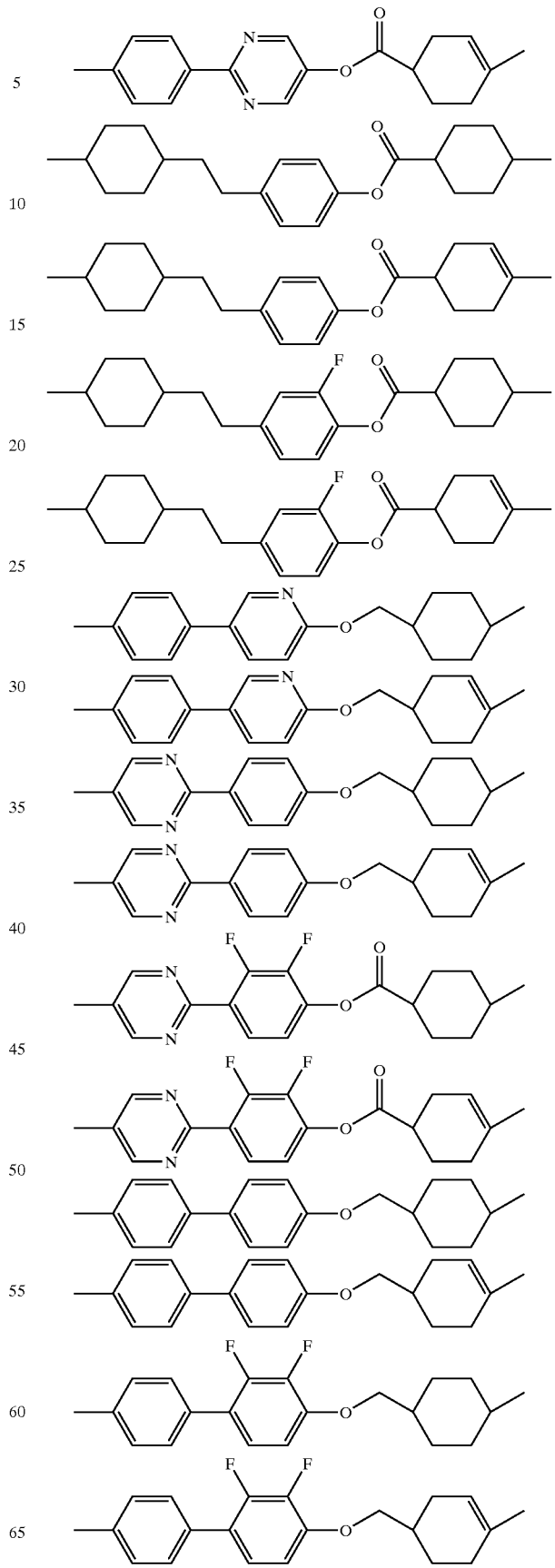

-continued

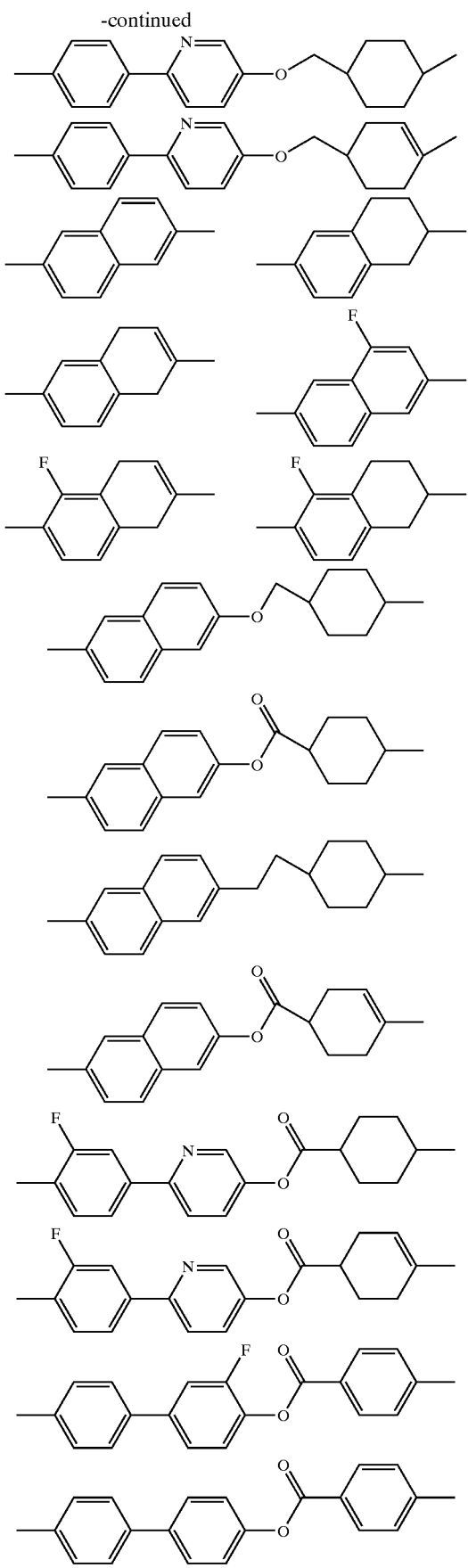

-continued

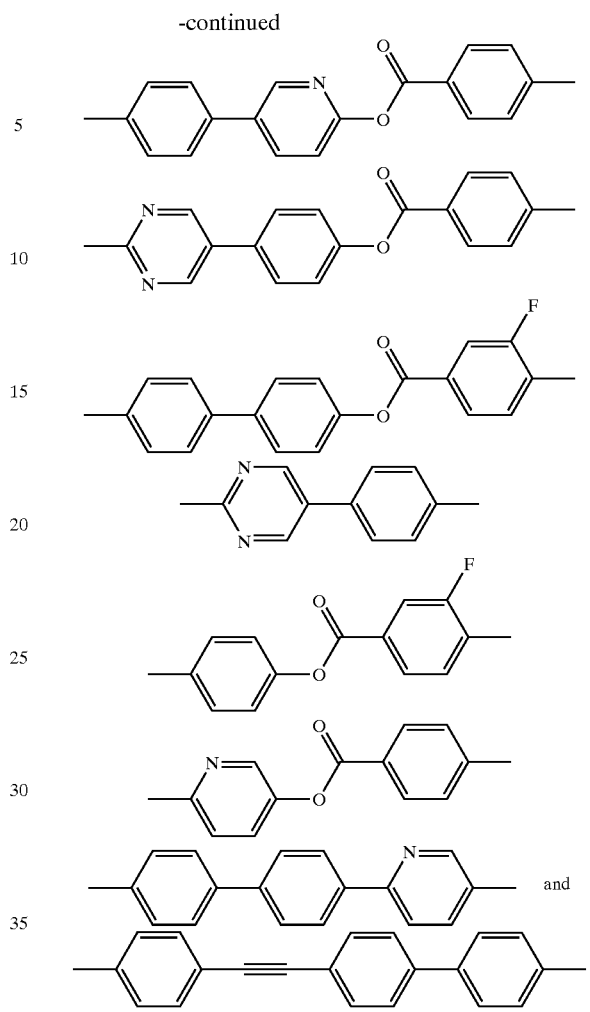

3. The liquid crystal composition of claim 1 wherein the core rings A, B and C are selected from the group consisting of phenyls, pyridines, pyrimidines and cyclohexanes.

4. The liquid crystal composition of claim 1 wherein the core is selected from the group consisting of biphenyl; dioxane; optionally substituted phenyl, optionally substituted cyclohexyl, optionally substituted cyclohexenyl, where one or more ring carbons is substituted with O, N or S; phenyl benzoate; phenylpyridine; and phenylpyrimidines.

5. The liquid crystal composition of claim 2 wherein $R_1$ is a straight-chain or branched alkyl or alkenyl group wherein one or more non-neighboring carbon atoms can be replaced with an oxygen atom and wherein one or more carbons can be substituted with one or more halogens.

6. The liquid crystal composition of claim 5 wherein $R_2$ and $R_3$, independently of one another, can be H, halogen or a lower alkyl or alkenyl group.

7. The liquid crystal composition of claim 6 wherein X is H, or a lower alkyl group.

8. The liquid crystal composition of claim 7 wherein Z is —O— or a single bond.

9. The liquid crystal composition of claim 8 wherein R is an ether, a partially fluorinated ether, or a perfluorinated ether.

10. The liquid crystal composition of claim 8 wherein R is $R^F$ and where $R^F$ is an achiral linear or branched perfluorinated or partially fluorinated alkyl group.

11. The liquid crystal composition of claim 10 wherein $R^F$ has the formula: $C_nF_{2n+1}C_mH_{2m}$ wherein n is an integer ranging from 1 to 20 and m is an integer ranging from 1 to 20.

12. The liquid crystal composition of claim 10 wherein $R^F$ has the formula: $C_nF_{2n+1}C_mH_{2m}$ wherein n is an integer ranging from 1 to 20 and m is an integer ranging from 0 to 20.

13. The liquid crystal composition of claim 7 wherein R is an achiral alkyl, alkenyl or alkynyl group having from 3 to 20 carbon atoms in which one or more of the non-neighboring carbons can be replaced with an oxygen, or in which one or more of the carbons is substituted with one of more halogens.

14. The liquid crystal composition of claim 8 wherein R is an achiral silane:

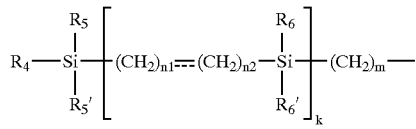

where:
R$^4$ is a straight chain or branched alkyl or alkenyl group having one or more carbon atoms and $R_5$, $R_{5'}$, $R_6$ and $R_{6'}$, independently of one another, are alkyl groups having from 1–6 carbon atoms;

n1 and m are integers from 1 to 20;

n2 can be zero or an integer from 1 to 20 where the dashed line indicates a possible double or triple bond;

k is 0 or an integer from 1 to 10.

15. The liquid crystal composition of claim 1 wherein R is $R^F$ and where $R^F$ is an achiral linear or branched perfluorinated or partially fluorinated alkyl group.

16. The liquid crystal composition of claim 15 wherein $R^F$ has the formula: $C_nF_{2n+1}C_mH_{2m}$ wherein n is an integer ranging from 1 to 10 and m is an integer ranging from 1 to 10.

17. The liquid crystal composition of claim 16 wherein $R^F$ is $C_4F_9C_4H_8$.

18. The liquid crystal composition of claim 17 wherein X is H.

19. The liquid crystal composition of claim 18 wherein the core is

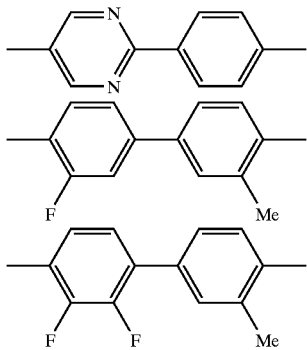

20. The liquid crystal composition of claim 19 wherein $R_1$ is $C_3H_7$.

21. The liquid crystal composition of claim 20 wherein X is H.

22. The liquid crystal composition of claim 20 wherein X is $CH_3$.

23. The liquid crystal composition of claim 1 having a Ps of at least 5 nC/cm$^2$.

24. The liquid crystal composition of claim 1 which exhibits a smectic C phase.

25. The liquid crystal composition of claim 1 which can be oriented within an achiral ferroelectric liquid crystal material.

26. A device comprising the liquid crystal composition of claim 1 oriented within an achiral ferroelectric liquid crystal layer exhibiting a smectic C Phase.

27. A liquid crystal compound having the formula:

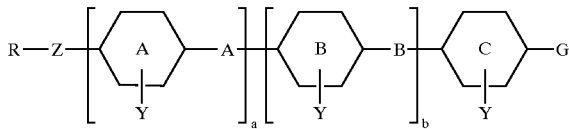

where the substituents between Z and G represent the core; where G is a chiral nonracemic optionally substituted α-ester γ-lactone of formula:

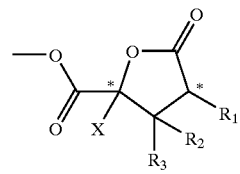

where * indicates a chiral carbon, $R_1$ is a straight-chain or branched alkyl or alkenyl group wherein one or more non-neighboring carbon atoms can be replaced with an oxygen atom and wherein one or more carbons can be substituted with one or more halogens;

$R_2$ and $R_3$, independently of one another, can be H, halogen or a lower alkyl or alkenyl group;

X is H, or a lower alkyl group;

R is selected from the group consisting of:
(1) an achiral straight chain or branched silane or siloxane having one or more silicon atoms and which may be substituted with one or more halogens
(2) an achiral linear or branched perfluorinated or partially fluorinated alkyl group ($R^F$);
(3) an achiral linear, cyclic or branched perfluorinated or partially fluorinated ether group;
(4) an achiral linear or branched ether having one or more oxygen atoms and which may be substituted with one or more halogens;
(5) an achiral alkyl, alkenyl or alkynyl group which may be substituted with one of more halogens; and
(6) or a straight chain or branched thioether having one or more sulfur atoms and which may be substituted with one or more halogens;

and where:
Z is a linker selected from the group consisting of O, CO, OOC, COO, S or a single bond;

core rings A, B and C can be aromatic or alicyclic, if aromatic, one or two ring carbons can be replaced with a nitrogen or if alicyclic rings can contain 3–10 carbon atoms and optionally can contain a double bond, wherein one or two $CH_2$ of the alicyclic ring can be replaced with a nitrogen, sulfur, or oxygen atom, or a C=O group;

Y represents up to four substituents on a given ring when the ring is aromatic and up to 20 substituents when the ring is alicyclic, where substituents are selected from halides, CN, $NO_2$, alkyl or alkoxy;

linkers A and B, independently, are selected from the group consisting of a single bond, —COO—, —OOC, —CH$_2$—CH$_2$—, —OCH$_2$—, —CH$_2$—O—, —CH═CH—(cis or trans); —C≡C—, and —CH═CH—CH═CH—(cis or trans);

and where a and b are integers that are 0 or 1 and where a+b is 1 or 2; wherein when X is H, R is not an achiral linear partially fluorinated ether group.

28. The liquid crystal compound of claim 27 wherein R is $R^F$.

29. The liquid crystal compound of claim 28 wherein $R^F$ has the formula: $C_nF_{2n+1}C_mH_{2m}$ wherein n is an integer ranging from 1 to 10 and m is an integer ranging from 1 to 10.

30. The liquid crystal compound of claim 29 wherein $R^F$ is $C_4F_9C_4H_8$.

31. The liquid crystal compound of claim 30 wherein X is H.

32. The liquid crystal compound of claim 31 wherein the core is

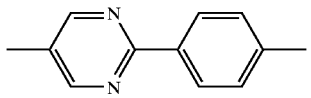

-continued

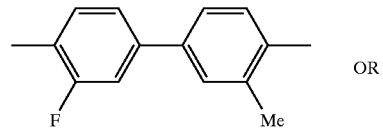

OR

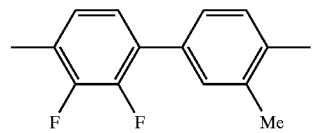

33. The liquid crystal compound of claim 32 wherein $R_1$ is $C_3H_7$.

34. The liquid crystal compound of claim 33 wherein X is H.

35. The liquid crystal compound of claim 34 wherein X is $CH_3$.

36. A liquid crystal compound having the formula:

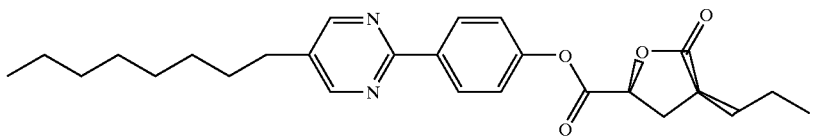

37. A liquid crystal compound having the formula:

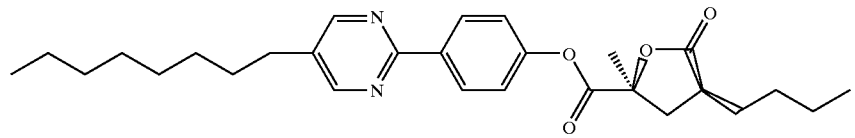

38. A liquid crystal compound having the formula:

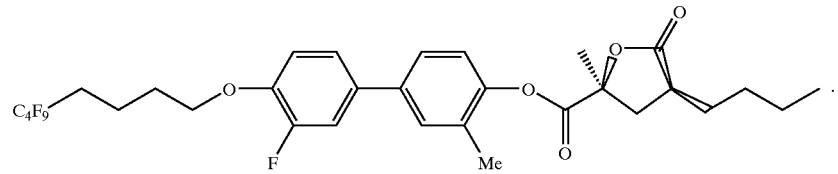

39. A liquid crystal compound having the formula:

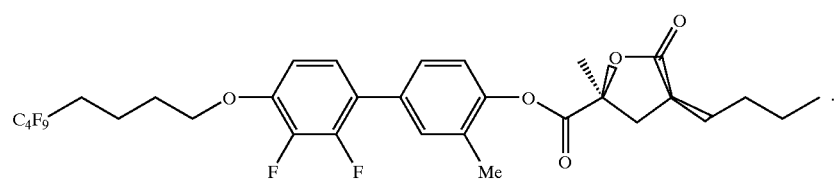

40. A liquid crystal device comprising a composition of one or more of the compounds of claim 27.

41. A ferroelectric liquid crystal device comprising an achiral smectic C liquid crystal host doped with from 1 to about 100% by weight of the compound of claim 27.

42. A ferroelectric liquid crystal device comprising an achiral smectic C liquid crystal host doped with from 1 to about 50% by weight of the compound of claim 27.

43. A ferroelectric liquid crystal device comprising an achiral smectic C liquid crystal host doped with from 1 to about 15% by weight of the compound of claim 27.

44. A polysiloxane having chiral mesogenic side chains, the polysiloxane having the formula:

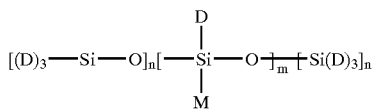

wherein D is an alkyl group having from 1 to 3 carbon atoms; n is either 0 or 1 and when y=0, m is a number ranging from 10 to 100 and when y=1, m is an integer ranging from 4 to 10 and wherein M is a chiral nonracemic mesogenic group having the formula:

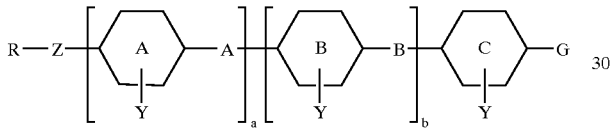

wherein where G is an optionally substituted α-ester γ-lactone having the formula:

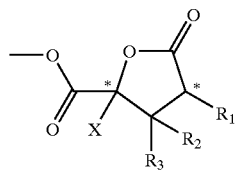

where $R_1$ is a straight-chain or branched alkyl or alkenyl group wherein one or more non-neighboring carbon atoms can be replaced with an oxygen atom and wherein one or more carbons can be substituted with one or more halogens;

$R_2$ and $R_3$, independently of one another, can be H, halogen or a lower alkyl or alkenyl group;

X is H, or a lower alkyl group;

where R is a straight chain alkyl group having from about 6 to about 12 carbon atoms; Z is O or a single bond;

core rings A, B and C can be aromatic or alicyclic; if aromatic one or two ring carbons can be replaced with a heteroatom; or if alicyclic, rings can contain 3–10 carbon atoms and optionally can contain a double bond, wherein one or two $CH_2$ of the alicyclic ring can be replaced with N, S, O or a C=O group;

Y represents up to four substituents on a given ring when the ring is aromatic and up to 0 substituents when the ring is alicyclic, where substituents are selected from halides, CN, $NO_2$, alkyl or alkoxy;

linkers A and B, independently, are selected from the group consisting of a single bond, —COO—, —OOC, —$CH_2$—$CH_2$—, —O$CH_2$—, —$CH_2$—O—, —CH=CH— (cis or trans); —C≡C—, —CH=CH—CH=CH— (cis or trans);

and where a and b are integers that are 0 or 1 and where a+b is 1 or 2.

* * * * *